US006429001B1

(12) United States Patent
Hardy

(10) Patent No.: US 6,429,001 B1
(45) Date of Patent: Aug. 6, 2002

(54) RECOMBINANT AAV PACKAGING SYSTEMS

(75) Inventor: Stephen F. Hardy, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/770,315

(22) Filed: Jan. 26, 2001

Related U.S. Application Data

(60) Provisional application No. 60/178,536, filed on Jan. 26, 2000.

(51) Int. Cl.[7] .......................... C12N 7/00; C12Q 1/68; C12P 21/06; C07H 21/04; A61K 39/12

(52) U.S. Cl. ....................... 435/235.1; 435/6; 435/69.1; 435/69.7; 536/23.72; 424/199.1

(58) Field of Search .......................... 435/6, 69.1, 69.7, 435/235.1; 536/23.72; 424/199.1

(56) References Cited

U.S. PATENT DOCUMENTS 5,622,856 A 4/1997 Natsoulis .................... 435/325
5,658,785 A 8/1997 Johnson ...................... 435/367
5,801,030 A 9/1998 McVey et al. ........... 435/172.3

FOREIGN PATENT DOCUMENTS

WO WO 94/13788 6/1995
WO WO 94/14771 6/1995

OTHER PUBLICATIONS

Ferrari et al., "New Developments in the Generation of Ad–free, High Titer rAAV Gene Therapy Vectors" *Nature Medicine 3* (11) :1295–1297, Nov., 1997.

Carter and Samulski, "Adeno–Associated Viral Vectors as Gene Delivery Vehicles (Review)" *International Journal Molecular Medicine 6*:17–27, 2000.

Tal, "Adeno–Associated Virus–Based Vectors in Gene Therapy" *Journal Biomedical Science 7*:279–291, 2000.

Bergemann et al., "Excision of Specific DNA–Sequences from Integrated Retroviral Vectors via Site–Specific Recombination" *Nucleic Acids Research 23*(21):4451–4456, 1995.

*Primary Examiner*—Hankyel T. Park

(74) *Attorney, Agent, or Firm*—Robert P. Blackburn; Louis Cullman; Anne S. Dollard

(57) ABSTRACT

Methods and compositions are provided for producing recombinant AAV vector particles; comprising the general steps of (a) introducing into a host cell (i) pfloxAAV, (ii) a recombinant viral vector encoding plasmid, and (iii) a plasmid encoding herpesvirus, cytomegalovirus, or adenoviral functions, or a herpesvirus, cytomegalovirus, or, adenovirus itself, in order to produce flox AAV particles and recombinant AAV particles; and (b) introducing into a second host cell (i) the recombinant AAV particles and flox AAV particles of (a), (ii) a vector which directs the expression of Cre, and (iii) a vector which directs the expression of herpesvirus, CMV, or adenovirus helper functions, such that said recombinant AAV vector particles are produced.

49 Claims, 13 Drawing Sheets cre/lox recombination and AAV

FIG. 5

Stable cell line vector production: loxP dependent

| | GFP functional titer ($x10^{-6}$/ml) | AAV packaged genomes($x10^{-10}$) |
|---|---|---|
| 309 | **250** | **50** |
| 309+Adcre | **8** | **ND** |
| 309 + loxP Adcre | **110** | **ND** |

ND = none detected, less than 5 $x10^9$/ml

FIG. 6

Transient vector production using floxAAV: evidence of feasibility

AAV vs. floxAAV plasmids to package GFP vector +/- Cre.

Packaged GFP (functional titers $x10^{-6}$/ml)

| | 293 | Cre |
|---|---|---|
| rep/cap | 15 | 15 |
| AAV | 3 | 3 |
| floxAAV | 16 | 15 |

Packaged AAV (particle titers $x10^{-10}$/ml)

| | 293 | Cre |
|---|---|---|
| rep/cap | ND | ND |
| AAV | 400 | 300 |
| floxAAV | 30 | 3 |

ND = none detected, $>1x10^9$/ml

E1 deleted adenovirus vector expressing Cre recombinase and containing a loxP site.

ΔE1 Cre-loxP adenovirus vector DNA

Full helper function adenovirus vector with Cre and loxP replacing E3 genes.

ΔE3 Cre-loxP adenovirus vector DNA

SEQUENCE LISTING

```
<160> NUMBER OF SEQ ID NOS: 8

<210> SEQ ID NO 1
<211> LENGTH: 7015
<212> TYPE: DNA
<213> ORGANISM: Unknown
<220> FEATURE:
<223> OTHER INFORMATION: recombinant DNA

<400> SEQUENCE: 1

gcgcgctcgc tcgctcactg aggccgcccg ggcaaagccc gggcgtcggg cgacctttgg     60

tcgcccggcc tcagtgagcg agcgagcgcg cagagaggga gtggccaact ccatcactga    120

taaaacttgc ggcccctcat cagggttagg aacattagag ccttgaatgg cagatttaat    180

accagcatca cccatgccta cagtattgtt atcggtagca agcacatcac cttgaatgcc    240

accggaggcg gctttttgac cgcctccaaa caatttagac atggcgccac cagcaagagc    300

agaagcaata ccgccagcaa tagcaccaaa cataaatcac ctcacttaag tggctggaga    360

caaataatct ctttaataac ctgattcagc gaaaccaatc cgcggcattt agtagcggta    420

aagttagacc aaaccatgaa accaacataa acgttattgc ccggcgtacg gggaaggacg    480

tcaatagtca cacagtcctt gacggtataa taaccaccat catggcgacc attcaaagga    540

taaacatcat aggcagtcgg gagggtagtc ggaaccgaag aagactcaaa gcgaaccaaa    600

caggcaaaaa atttagggtc ggcatcaaaa gcaatatcag caccaacaga aacaacctga    660

ttagcggcgt tgacagatgt atccatctga atgcaatgaa gaaaaccacc attaccagca    720

ttaaccgtca aactatcaaa atataacgtt gacgatgtag ctttaggtgt ctgtaaaaca    780

ggtgccgaag aagctggagt aacagaagtg agaaccagct tatcagaaaa aaagtttgaa    840

ttatggcgag aaataaaagt ctgaaacatg attaaactcc taagcagaaa acctaccgcg    900

cttcgcttgg tcaacccctc agcggcaaaa attaaaattt ttaccgcttc ggcgttataa    960

cctcacactc aatcttttat cacgaagtca tgattgaatc gcgagtggtc ggcagattgc   1020

gataaacggt cacattaaat ttaacctgac tattccactg caacaactga acggactgga   1080

aacactggtc ataatcatgg tggcgaataa gtacgcgttc ttgcaaatca ccagaaggcg   1140

gttcctgaat gaatgggaag ccttcaagaa ggtgataagc aggagaaaca tacgaaggcg   1200

cataacgata ccactgaccc tcagcaatct taaacttctt agacgaatca ccagaacgga   1260

aaacatcctt catagaaatt tcacgcggcg gcaagttgcc atacaaaaca gggtcgccag   1320

caatatcggt ataagtcaaa gcacctttag cgttaaggta ctgaatctct ttagtcgcag   1380

taggcggaaa acgaacaagc gcaagagtaa acatagtgcc atgctcagga acaaagaaac   1440

gcggcacaga atgtttatag gtctgttgaa cacgaccaga aaactggggc cgcggaattt   1500
```

-continued

```
cgactctagg ccattgcata cgttgtatct atatcataat atgtacattt atattggctc   1560
atgtccaata tgaccgccat gttgacattg attattgact agttattaat agtaatcaat   1620
tacggggtca ttagttcata gcccatatat ggagttccgc gttacataac ttacggtaaa   1680
tggcccgcct ggctgaccgc ccaacgaccc ccgcccattg acgtcaataa tgacgtatgt   1740
tcccatagta acgccaatag ggactttcca ttgacgtcaa tgggtggagt atttacggta   1800
aactgcccac ttggcagtac atcaagtgta tcatatgcca agtccgcccc ctattgacgt   1860
caatgacggt aaatggcccg cctggcatta tgcccagtac atgaccttac gggactttcc   1920
tacttggcag tacatctacg tattagtcat cgctattacc atggtgatgc ggttttggca   1980
gtacaccaat gggcgtggat agcggtttga ctcacgggga tttccaagtc tccaccccat   2040
tgacgtcaat gggagtttgt tttggcacca aaatcaacgg gactttccaa aatgtcgtaa   2100
taaccccgcc ccgttgacgc aaatgggcgg taggcgtgta cggtgggagg tctatataag   2160
cagagctcgt ttagtgaacc gtcagatcgc ctggagacgc catccacgct gttttgacct   2220
ccatagaaga caccgggacc gatccagcct ccgcggccgg gaacggtgca ttggaacgcg   2280
gattccccgt gccaagagtg acgtaagtac cgcctataga ctctataggc acacccottt   2340
ggctcttatg catgctatac tgtttttggc ttggggccta tacacccccg ctccttatgc   2400
tataggtgat ggtatagctt agcctatagg tgtgggttat tgaccattat tgaccactcc   2460
cctattggtg acgatacttt ccattactaa tccataacat ggctctttgc cacaactatc   2520
tctattggct atatgccaat actctgtcct tcagagactg acacggactc tgtattttta   2580
caggatgggg tccatttatt atttacaaat tcacatatac aacaacgccg tcccccgtgc   2640
ccgcagtttt tattaaacat agcgtgggat ctccgacatc tcgggtacgt gttccggaca   2700
tgggctcttc tccggtagcg gcggagcttc cacatccgag ccctggtccc atccgtccag   2760
cggctcatgg tcgctcggca gctccttgct cctaacagtg gaggccagac ttaggcacag   2820
cacaatgccc accaccacca gtgtgccgca caaggccgtg gcggtagggt atgtgtctga   2880
aaatgagctc ggagattggg ctcgcacctg gacgcagatg gaagacttaa ggcagcggca   2940
gaagaagatg caggcagctg agttgttgta ttctgataag agtcagaggt aactcccgtt   3000
gcggtgctgt taacggtgga gggcagtgta gtctgagcag tactcgttgc tgccgcgcgc   3060
gccaccagac ataatagctg acagactaac agactgttcc tttccatggg tcttttctgc   3120
agtcaccgtc gtcgacggta ccgcgggccc gggatccacc ggtcgccacc atggtgagca   3180
agggcgagga gctgttcacc ggggtggtgc ccatcctggt cgagctggac ggcgacgtaa   3240
acggccacaa gttcagcgtg tccggcgagg gcgagggcga tgccacctac ggcaagctga   3300
ccctgaagtt catctgcacc accggcaagc tgcccgtgcc ctggcccacc ctcgtgacca   3360
ccctgaccta cggcgtgcag tgcttcagcc gctaccccga ccacatgaag cagcacgact   3420
tcttcaagtc cgccatgccc gaaggctacg tccaggagcg caccatcttc ttcaaggacg   3480
acggcaacta caagacccgc gccgaggtga agttcgaggg cgacaccctg gtgaaccgca   3540
tcgagctgaa gggcatcgac ttcaaggagg acggcaacat cctggggcac aagctggagt   3600
acaactacaa cagccacaac gtctatatca tggccgacaa gcagaagaac ggcatcaagg   3660
tgaacttcaa gatccgccac aacatcgagg acggcagcgt gcagctcgcc gaccactacc   3720
agcagaacac ccccatcggc gacggccccg tgctgctgcc cgacaaccac tacctgagca   3780
cccagtccgc cctgagcaaa gaccccaacg agaagcgcga tcacatggtc ctgctggagt   3840
tcgtgaccgc cgccgggatc actctcggca tggacgagct gtacaagtaa agcggccgcg   3900
```

-continued

```
actctagaaa gccatggata tcggatccac tacgcgttag agctcgctga tcagcctcga   3960
ctgtgccttc tagttgccag ccatctgttg tttgcccctc ccccgtgcct tccttgaccc   4020
tggaaggtgc cactcccact gtcctttcct aataaaatga ggaaattgca tcgcattgtc   4080
tgagtaggtg tcattctatt ctggggggtg gggtggggca ggacagcaag ggggaggatt   4140
gggaagacaa tagcaggggg gtgggcgaag aactccagca tgagatcccc gcgctggagg   4200
atcatccagc tagcaagtcc catcagtgat ggagttggcc actccctctc tgcgcgctcg   4260
ctcgctcact gaggccgggc gaccaaaggt cgcccgacgc ccgggctttg cccgggcggc   4320
ctcagtgagc gagcgagcgc gccagcgatt ctcttgtttg ctccagactc tcaggcaatg   4380
acctgatagc ctttgtagag acctctcaaa aatagctacc ctctccggca tgaatttatc   4440
agctagaacg gttgaatatc atattgatgg tgatttgact gtctccggcc tttctcaccc   4500
gtttgaatct ttacctacac attactcagg cattgcattt aaaatatatg agggttctaa   4560
aaatttttat ccttgcgttg aaataaaggc ttctcccgca aaagtattac agggtcataa   4620
tgtttttggt acaaccgatt tagctttatg ctctgaggct ttattgctta attttgctaa   4680
ttctttgcct tgcctgtatg atttattgga tgttggaatt cctgatgcgg tattttctcc   4740
ttacgcatct gtgcggtatt tcacaccgca tatggtgcac tctcagtaca atctgctctg   4800
atgccgcata gttaagccag ccccgacacc cgccaacacc cgctgacgcg ccctgacggg   4860
cttgtctgct cccggcatcc gcttacagac aagctgtgac cgtctccggg agctgcatgt   4920
gtcagaggtt ttcaccgtca tcaccgaaac gcgcgagacg aaagggcctc gtgatacgcc   4980
tatttttata ggttaatgtc atgataataa tggtttctta gacgtcaggt ggcacttttc   5040
ggggaaatgt gcgcggaacc cctatttgtt tatttttcta aatacattca aatatgtatc   5100
cgctcatgag acaataaccc tgataaatgc ttcaataata ttgaaaaagg aagagtatga   5160
gtattcaaca tttccgtgtc gcccttattc ccttttttgc ggcattttgc cttcctgttt   5220
ttgctcaccc agaaacgctg gtgaaagtaa aagatgctga agatcagttg ggtgcacgag   5280
tgggttacat cgaactggat ctcaacagcg gtaagatcct tgagagtttt cgccccgaag   5340
aacgttttcc aatgatgagc acttttaaag ttctgctatg tggcgcggta ttatcccgta   5400
ttgacgccgg gcaagagcaa ctcggtcgcc gcatacacta ttctcagaat gacttggttg   5460
agtactcacc agtcacagaa aagcatctta cggatggcat gacagtaaga gaattatgca   5520
gtgctgccat aaccatgagt gataacactg cggccaactt acttctgaca acgatcggag   5580
gaccgaagga gctaaccgct tttttgcaca acatggggga tcatgtaact cgccttgatc   5640
gttgggaacc ggagctgaat gaagccatac caaacgacga gcgtgacacc acgatgcctg   5700
tagcaatggc aacaacgttg cgcaaactat taactggcga actacttact ctagcttccc   5760
ggcaacaatt aatagactgg atggaggcgg ataaagttgc aggaccactt ctgcgctcgg   5820
cccttccggc tggctggttt attgctgata aatctggagc cggtgagcgt gggtctcgcg   5880
gtatcattgc agcactgggg ccagatggta agccctcccg tatcgtagtt atctacacga   5940
cggggagtca ggcaactatg gatgaacgaa atagacagat cgctgagata ggtgcctcac   6000
tgattaagca ttggtaactg tcagaccaag tttactcata tatactttag attgatttaa   6060
aacttcattt ttaatttaaa aggatctagg tgaagatcct ttttgataat ctcatgacca   6120
aaatccctta acgtgagttt tcgttccact gagcgtcaga ccccgtagaa aagatcaaag   6180
gatcttcttg agatcctttt tttctgcgcg taatctgctg cttgcaaaca aaaaaaccac   6240
```

-continued

```
cgctaccagc ggtggtttgt ttgccggatc aagagctacc aactcttttt ccgaaggtaa   6300

ctggcttcag cagagcgcag ataccaaata ctgtccttct agtgtagccg tagttaggcc   6360

accacttcaa gaactctgta gcaccgccta catacctcgc tctgctaatc ctgttaccag   6420

tggctgctgc cagtggcgat aagtcgtgtc ttaccgggtt ggactcaaga cgatagttac   6480

cggataaggc gcagcggtcg ggctgaacgg ggggttcgtg cacacagccc agcttggagc   6540

gaacgaccta caccgaactg agatacctac agcgtgagct atgagaaagc gccacgcttc   6600

ccgaagggag aaaggcggac aggtatccgg taagcggcag ggtcggaaca ggagagcgca   6660

cgagggagct tccaggggga aacgcctggt atctttatag tcctgtcggg tttcgccacc   6720

tctgacttga gcgtcgattt ttgtgatgct cgtcaggggg gcggagccta tggaaaaacg   6780

ccagcaacgc ggccttttta cggttcctgg ccttttgctg gccttttgct cacatgttct   6840

ttcctgcgtt atcccctgat tctgtggata accgtattac cgcctttgag tgagctgata   6900

ccgctcgccg cagccgaacg accgagcgca gcgagtcagt gagcgaggaa gcggaagagc   6960

gcccaatacg caaaccgcct ctccccgcgc gttggccgat tcattaatgc agctg        7015
```

<210> SEQ ID NO 2
<211> LENGTH: 8698
<212> TYPE: DNA
<213> ORGANISM: Unknown
<220> FEATURE:
<223> OTHER INFORMATION: recombinant DNA

<400> SEQUENCE: 2

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180

ggttagggag gtcctgtatt agaggtcacg tgagtgtttt gcgacatttt gcgacaccat    240

gtggtcacgc tgggtattta agcccgagtg agcacgcagg gtctccattt tgaagcggga    300

ggtttgaacg cgcagccgcc atgccggggt tttacgagat tgtgattaag gtccccagcg    360

accttgacga gcatctgccc ggcatttctg acagctttgt gaactgggtg gccgagaagg    420

aatgggagtt gccgccagat tctgacatgg atctgaatct gattgagcag gcacccctga    480

ccgtggccga gaagctgcag cgcgactttc tgacggaatg gcgccgtgtg agtaaggccc    540

cggaggccct tttctttgtg caatttgaga agggagagag ctacttccac atgcacgtgc    600

tcgtggaaac caccggggtg aaatccatgg ttttgggacg tttcctgagt cagattcgcg    660

aaaaactgat tcagagaatt taccgcggga tcgagccgac tttgccaaac tggttcgcgg    720

tcacaaagac cagaaatggc gccggaggcg ggaacaaggt ggtggatgag tgctacatcc    780

ccaattactt gctccccaaa acccagcctg agctccagtg ggcgtggact aatatggaac    840

agtatttaag cgcctgtttg aatctcacgg agcgtaaacg gttggtggcg cagcatctga    900

cgcacgtgtc gcagacgcag gagcagaaca aagagaatca gaatcccaat tctgatgcgc    960

cggtgatcag atcaaaaact tcagccaggt acatggagct ggtcgggtgg ctcgtggaca   1020

aggggattac ctcggagaag cagtggatcc aggaggacca ggcctcatac atctccttca   1080

atgcggcctc caactcgcgg tcccaaatca aggctgcctt ggacaatgcg ggaaagatta   1140

tgagcctgac taaaaccgcc cccgactacc tggtgggcca gcagcccgtg gaggacattt   1200

ccagcaatcg gatttataaa attttggaac taaacgggta cgatccccaa tatgcggctt   1260

ccgtctttct gggatgggcc acgaaaaagt tcggcaagag gaacaccatc tggctgtttg   1320
```

-continued

```
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agactttttc cggtgggcaa   1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt ttcaggagcg ccttaaagaa   2520
gatacgtctt ttgggggcaa cctcggacga gcagtcttcc aggcgaaaaa gagggttctt   2580
gaacctctgg gcctggttga ggaacctgtt aagacggctc cgggaaaaaa gaggccggta   2640
gagcactctc ctgtggagcc agactcctcc tcgggaaccg gaaaggcggg ccagcagcct   2700
gcaagaaaaa gattgaattt tggtcagact ggagacgcag actcagtacc tgacccccag   2760
cctctcggac agccaccagc agccccctct ggtctgggaa ctaatacgat ggctacaggc   2820
agtggcgcac caatggcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg gaccctgtta ccgccagcag   3660
```

-continued

```
cgagtatcaa agacatctgc ggataacaac aacagtgaat actcgtggac tggagctacc   3720
aagtaccacc tcaatggcag agactctctg gtgaatccgg gcccggccat ggcaagccac   3780
aaggacgatg aagaaaagtt ttttcctcag agcggggttc tcatctttgg gaagcaaggc   3840
tcagagaaaa caaatgtgga cattgaaaag gtcatgatta cagacgaaga ggaaatcagg   3900
acaaccaatc ccgtggctac ggagcagtat ggttctgtat ctaccaacct ccagagaggc   3960
aacagacaag cagctaccgc agatgtcaac acacaaggcg ttcttccagg catggtctgg   4020
caggacagag atgtgtacct tcaggggccc atctgggcaa agattccaca cacggacgga   4080
cattttcacc cctctcccct catgggtgga ttcggactta aacaccctcc tccacagatt   4140
ctcatcaaga acaccccggt acctgcgaat ccttcgacca ccttcagtgc ggcaaagttt   4200
gcttccttca tcacacagta ctccacggga caggtcagcg tggagatcga gtgggagctg   4260
cagaaggaaa acagcaaacg ctggaatccc gaaattcagt acacttccaa ctacaacaag   4320
tctgttaatg tggactttac tgtggacact aatggcgtgt attcagagcc tcgccccatt   4380
ggcaccagat acctgactcg taatctgtaa ttgcttgtta atcaataaac cgtttaattc   4440
gtttcagttg aactttggtc tctgcgtatt tctttcttat ctagtttcca tggctacgta   4500
gataagtagc atggcgggtt aatcattaac tacaaggaac ccctagtgat ggagttggcc   4560
actccctctc tgcgcgctcg ctcgctcact gaggccgggc gaccaaaggt cgcccgacgc   4620
ccgggctttg cccgggcggc ctcagtgagc gagcgagcgc gcagagaggg agtggccaaa   4680
gatcttctag agatcctcta cgccggacgc atcgtggccg gcatcaccgg cgccacaggt   4740
gcggttgctg gcgcctatat cgccgacatc accgatgggg aagatcgggc tcgccacttc   4800
gggctcatga gcgcttgttt cggcgtgggt atggtggcag gccccgtggc cgggggactg   4860
ttgggcgcca tctccttgca tgcaccattc cttgcggcgg cggtgctcaa cggcctcaac   4920
ctactactgg gctgcttcct aatgcaggag tcgcataagg gagagcgtcg accgatgccc   4980
ttgagagcct tcaacccagt cagctccttc cggtgggcgc ggggcatgac tatcgtcgcc   5040
gcacttatga ctgtcttctt tatcatgcaa ctcgtaggac aggtgccggc agcgctctgg   5100
gtcattttcg gcgaggaccg ctttcgctgg agcgcgacga tgatcggcct gtcgcttgcg   5160
gtattcggaa tcttgcacgc cctcgctcaa gccttcgtca ctggtcccgc caccaaacgt   5220
ttcggcgaga agcaggccat tatcgccggc atggcggccg acgcgctggg ctacgtcttg   5280
ctggcgttcg cgacgcgagg ctggatggcc ttccccatta tgattcttct cgcttccggc   5340
ggcatcggga tgcccgcgtt gcaggccatg ctgtccaggc aggtagatga cgaccatcag   5400
ggacagcttc aaggatcgct cgcggctctt accagcctaa cttcgatcac tggaccgctg   5460
atcgtcacgg cgatttatgc cgcctcggcg agcacatgga acgggttggc atggattgta   5520
ggcgccgccc tataccttgt ctgcctcccc gcgttgcgtc gcggtgcatg gagccgggcc   5580
acctcgacct gaatggaagc cggcggcacc tcgctaacgg attcaccact ccaagaattg   5640
gagccaatca attcttgcgg agaactgtga atgcgcaaac caacccttgg cagaacatat   5700
ccatcgcgtc cgccatctcc agcagccgca cgcggcgcat ctcgggcagc gttgggtcct   5760
ggccacgggt gcgcatgatc gtgctcctgt cgttgaggac ccggctaggc tggcggggtt   5820
gccttactgg ttagcagaat gaatcaccga tacgcgagcg aacgtgaagc gactgctgct   5880
gcaaaacgtc tgcgacctga gcaacaacat gaatggtctt cggtttccgt gtttcgtaaa   5940
gtctggaaac gcggaagtca gcgccctgca ccattatgtt ccggatctgc atcgcaggat   6000
gctgctggct accctgtgga acacctacat ctgtattaac gaagcgctgg cattgaccct   6060
```

-continued

```
gagtgatttt tctctggtcc cgccgcatcc ataccgccag ttgtttaccc tcacaacgtt   6120
ccagtaaccg ggcatgttca tcatcagtaa cccgtatcgt gagcatcctc tctcgtttca   6180
tcggtatcat tacccccatg aacagaaatc cccttacac ggaggcatca gtgaccaaac   6240
aggaaaaaac cgcccttaac atggcccgct ttatcagaag ccagacatta acgcttctgg   6300
agaaactcaa cgagctggac gcggatgaac aggcagacat ctgtgaatcg cttcacgacc   6360
acgctgatga gctttaccgc agctgcctcg cgcgtttcgg tgatgacggt gaaaacctct   6420
gacacatgca gctcccggag acggtcacag cttgtctgta agcggatgcc gggagcagac   6480
aagcccgtca gggcgcgtca gcgggtgttg gcgggtgtcg gggcgcagcc atgacccagt   6540
cacgtagcga tagcggagtg tatactggct taactatgcg gcatcagagc agattgtact   6600
gagagtgcac catatgcggt gtgaaatacc gcacagatgc gtaaggagaa aataccgcat   6660
caggcgctct tccgcttcct cgctcactga ctcgctgcgc tcggtcgttc ggctgcggcg   6720
agcggtatca gctcactcaa aggcggtaat acggttatcc acagaatcag gggataacgc   6780
aggaaagaac atgtgagcaa aaggccagca aaaggccagg aaccgtaaaa aggccgcgtt   6840
gctggcgttt ttccataggc tccgcccccc tgacgagcat cacaaaaatc gacgctcaag   6900
tcagaggtgg cgaaacccga caggactata aagataccag gcgtttcccc ctggaagctc   6960
cctcgtgcgc tctcctgttc cgaccctgcc gcttaccgga tacctgtccg cctttctccc   7020
ttcgggaagc gtggcgcttt ctcatagctc acgctgtagg tatctcagtt cggtgtaggt   7080
cgttcgctcc aagctgggct gtgtgcacga accccccgtt cagcccgacc gctgcgcctt   7140
atccggtaac tatcgtcttg agtccaaccc ggtaagacac gacttatcgc cactggcagc   7200
agccactggt aacaggatta gcagagcgag gtatgtaggc ggtgctacag agttcttgaa   7260
gtggtggcct aactacggct acactagaag gacagtattt ggtatctgcg ctctgctgaa   7320
gccagttacc ttcggaaaaa gagttggtag ctcttgatcc ggcaaacaaa ccaccgctgg   7380
tagcggtggt ttttttgttt gcaagcagca gattacgcgc agaaaaaaag gatctcaaga   7440
agatcctttg atcttttcta cggggtctga cgctcagtgg aacgaaaact cacgttaagg   7500
gattttggtc atgagattat caaaaaggat cttcacctag atccttttaa attaaaaatg   7560
aagttttaaa tcaatctaaa gtatatatga gtaaacttgg tctgacagtt accaatgctt   7620
aatcagtgag gcacctatct cagcgatctg tctatttcgt tcatccatag ttgcctgact   7680
ccccgtcgtg tagataacta cgatacggga gggcttacca tctggcccca gtgctgcaat   7740
gataccgcga gacccacgct caccggctcc agatttatca gcaataaacc agccagccgg   7800
aagggccgag cgcagaagtg gtcctgcaac tttatccgcc tccatccagt ctattaattg   7860
ttgccgggaa gctagagtaa gtagttcgcc agttaatagt ttgcgcaacg ttgttgccat   7920
tgctgcaggc atcgtggtgt cacgctcgtc gtttggtatg gcttcattca gctccggttc   7980
ccaacgatca aggcgagtta catgatcccc catgttgtgc aaaaaagcgg ttagctcctt   8040
cggtcctccg atcgttgtca gaagtaagtt ggccgcagtg ttatcactca tggttatggc   8100
agcactgcat aattctctta ctgtcatgcc atccgtaaga tgcttttctg tgactggtga   8160
gtactcaacc aagtcattct gagaatagtg tatgcggcga ccgagttgct cttgcccggc   8220
gtcaacacgg gataataccg cgccacatag cagaacttta aaagtgctca tcattggaaa   8280
acgttcttcg gggcgaaaac tctcaaggat cttaccgctg ttgagatcca gttcgatgta   8340
acccactcgt gcacccaact gatcttcagc atcttttact ttcaccagcg tttctgggtg   8400
```

-continued

```
agcaaaaaca ggaaggcaaa atgccgcaaa aaagggaata agggcgacac ggaaatgttg   8460

aatactcata ctcttccttt ttcaatatta ttgaagcatt tatcagggtt attgtctcat   8520

gagcggatac atatttgaat gtatttagaa aaataaacaa ataggggttc cgcgcacatt   8580

tccccgaaaa gtgccacctg acgtctaaga aaccattatt atcatgacat taacctataa   8640

aaataggcgt atcacgaggc cctttcgtct tcaagaattc ggatccctgc agagatct     8698


<210> SEQ ID NO 3
<211> LENGTH: 7557
<212> TYPE: DNA
<213> ORGANISM: Unknown
<220> FEATURE:
<223> OTHER INFORMATION: recombinant DNA

<400> SEQUENCE: 3

ctggcgcgct cgctcgctca ctgaggccgc ccgggcaaag cccgggcgtc gggcgacctt     60

tggtcgcccg gcctcagtga gcgagcgagc gcgcagagag ggagtggcca actccatcac    120

tgatgggact tgctagcata acttcgtata atgtatgcta tacgaagtta tccggagggg    180

tggagtcgtg acgtgaatta cgtcataggg ttagggaggt cctgtattag aggtcacgtg    240

agtgttttgc gacattttgc gacaccatgt ggtcacgctg ggtatttaag cccgagtgag    300

cacgcagggt ctccattttg aagcgggagg tttgaacgcg cagccgccat gccggggttt    360

tacgagattg tgattaaggt ccccagcgac cttgacgagc atctgcccgg catttctgac    420

agctttgtga actgggtggc cgagaaggaa tgggagttgc cgccagattc tgacatggat    480

ctgaatctga ttgagcaggc acccctgacc gtggccgaga agctgcagcg cgactttctg    540

acggaatggc gccgtgtgag taaggccccg gaggcccttt tctttgtgca atttgagaag    600

ggagagagct acttccacat gcacgtgctc gtggaaacca ccggggtgaa atccatggtt    660

ttgggacgtt tcctgagtca gattcgcgaa aaactgattc agagaattta ccgcgggatc    720

gagccgactt tgccaaactg gttcgcggtc acaaagacca gaaatggcgc cggaggcggg    780

aacaaggtgg tggatgagtg ctacatcccc aattacttgc tccccaaaac ccagcctgag    840

ctccagtggg cgtggactaa tatggaacag tatttaagcg cctgtttgaa tctcacggag    900

cgtaaacggt tggtggcgca gcatctgacg cacgtgtcgc agacgcagga gcagaacaaa    960

gagaatcaga atcccaattc tgatgcgccg gtgatcagat caaaaacttc agccaggtac   1020

atggagctgg tcgggtggct cgtggacaag gggattacct cggagaagca gtggatccag   1080

gaggaccagg cctcatacat ctccttcaat gcggcctcca actcgcggtc ccaaatcaag   1140

gctgccttgg acaatgcggg aaagattatg agcctgacta aaaccgcccc cgactacctg   1200

gtgggccagc agcccgtgga ggacatttcc agcaatcgga tttataaaat tttggaacta   1260

aacgggtacg atccccaata tgcggcttcc gtctttctgg gatgggccac gaaaaagttc   1320

ggcaagagga acaccatctg gctgtttggg cctgcaacta ccgggaagac caacatcgcg   1380

gaggccatag cccacactgt gcccttctac gggtgcgtaa actggaccaa tgagaacttt   1440

cccttcaacg actgtgtcga caagatggtg atctggtggg aggaggggaa gatgaccgcc   1500

aaggtcgtgg agtcggccaa agccattctc ggaggaagca aggtgcgcgt ggaccagaaa   1560

tgcaagtcct cggcccagat agacccgact cccgtgatcg tcacctccaa caccaacatg   1620

tgcgccgtga ttgacgggaa ctcaacgacc ttcgaacacc agcagccgtt gcaagaccgg   1680

atgttcaaat ttgaactcac ccgccgtctg gatcatgact ttgggaaggt caccaagcag   1740

gaagtcaaag actttttccg gtgggcaaag gatcacgtgg ttgaggtgga gcatgaattc   1800
```

-continued

```
tacgtcaaaa agggtggagc caagaaaaga cccgcccccca gtgacgcaga tataagtgag   1860
cccaaacggg tgcgcgagtc agttgcgcag ccatcgacgt cagacgcgga agcttcgatc   1920
aactacgcag acaggtacca aaacaaatgt tctcgtcacg tgggcatgaa tctgatgctg   1980
tttccctgca gacaatgcga gagaatgaat cagaattcaa atatctgctt cactcacgga   2040
cagaaagact gtttagagtg ctttcccgtg tcagaatctc aacccgtttc tgtcgtcaaa   2100
aaggcgtatc agaaactgtg ctacattcat catatcatgg gaaaggtgcc agacgcttgc   2160
actgcctgcg atctggtcaa tgtggatttg gatgactgca tctttgaaca ataaatgatt   2220
taaatcaggt atggctgccg atggttatct tccagattgg ctcgaggaca ctctctctga   2280
aggaataaga cagtggtgga agctcaaacc tggcccacca ccaccaaagc ccgcagagcg   2340
gcataaggac gacagcaggg gtcttgtgct tcctgggtac aagtacctcg gacccttcaa   2400
cggactcgac aagggagagc cggtcaacga ggcagacgcc gcggccctcg agcacgacaa   2460
agcctacgac cggcagctcg acagcggaga caacccgtac ctcaagtaca accacgccga   2520
cgcggagttt caggagcgcc ttaaagaaga tacgtctttt gggggcaacc tcggacgagc   2580
agtcttccag gcgaaaaaga gggttcttga acctctgggc ctggttgagg aacctgttaa   2640
gacggctccg ggaaaaaaga ggccggtaga gcactctcct gtggagccag actcctcctc   2700
gggaaccgga aaggcgggcc agcagcctgc aagaaaaaga ttgaattttg gtcagactgg   2760
agacgcagac tcagtacctg acccccagcc tctcggacag ccaccagcag ccccctctgg   2820
tctgggaact aatacgatgg ctacaggcag tggcgcacca atggcagaca ataacgaggg   2880
cgccgacgga gtgggtaatt cctcgggaaa ttggcattgc gattccacat ggatgggcga   2940
cagagtcatc accaccagca cccgaacctg ggccctgccc acctacaaca accacctcta   3000
caaacaaatt tccagccaat caggagcctc gaacgacaat cactactttg gctacagcac   3060
cccttggggg tattttgact tcaacagatt ccactgccac ttttcaccac gtgactggca   3120
aagactcatc aacaacaact ggggattccg acccaagaga ctcaacttca agctctttaa   3180
cattcaagtc aaagaggtca cgcagaatga cggtacgacg acgattgcca ataaccttac   3240
cagcacggtt caggtgttta ctgactcgga gtaccagctc ccgtacgtcc tcggctcggc   3300
gcatcaagga tgcctcccgc cgttcccagc agacgtcttc atggtgccac agtatggata   3360
cctcaccctg aacaacggga gtcaggcagt aggacgctct tcattttact gcctggagta   3420
ctttccttct cagatgctgc gtaccggaaa caactttacc ttcagctaca cttttgagga   3480
cgttcctttc cacagcagct acgctcacag ccagagtctg gaccgtctca tgaatcctct   3540
catcgaccag tacctgtatt acttgagcag aacaaacact ccaagtggaa ccaccacgca   3600
gtcaaggctt cagttttctc aggccggagc gagtgacatt cgggaccagt ctaggaactg   3660
gcttcctgga ccctgttacc gccagcagcg agtatcaaag acatctgcgg ataacaacaa   3720
cagtgaatac tcgtggactg gagctaccaa gtaccacctc aatggcagag actctctggt   3780
gaatccgggc ccggccatgg caagccacaa ggacgatgaa gaaaagtttt ttcctcagag   3840
cggggttctc atctttggga agcaaggctc agagaaaaca aatgtggaca ttgaaaaggt   3900
catgattaca gacgaagagg aaatcaggac aaccaatccc gtggctacgg agcagtatgg   3960
ttctgtatct accaacctcc agagaggcaa cagacaagca gctaccgcag atgtcaacac   4020
acaaggcgtt cttccaggca tggtctggca ggacagagat gtgtaccttc aggggcccat   4080
ctgggcaaag attccacaca cggacggaca ttttcacccc tctcccctca tgggtggatt   4140
```

-continued

```
cggacttaaa caccctcctc cacagattct catcaagaac accccggtac ctgcgaatcc   4200
ttcgaccacc ttcagtgcgg caaagtttgc ttccttcatc acacagtact ccacgggaca   4260
ggtcagcgtg gagatcgagt gggagctgca gaaggaaaac agcaaacgct ggaatcccga   4320
aattcagtac acttccaact acaacaagtc tgttaatgtg gactttactg tggacactaa   4380
tggcgtgtat tcagagcctc gccccattgg caccagatac ctgactcgta atctgtaatt   4440
gcttgttaat caataaaccg tttaattcgt ttcagttgaa ctttggtctc tgcgtatttc   4500
tttcttatct agtttccatg gctacgtaga taagtagcat ggcgggttaa tcattaacta   4560
gtataacttc gtataatgta tgctatacga agttatacgc gtgccatgtc taaattgttt   4620
ggaggcggtc aaaaagccgc ctccggtggc attcaaggtg atgtgcttgc taccgataac   4680
aatactgtag gcatgggtga tgctggtatt aaatctgcca ttcaaggctc taatgttcct   4740
aaccctgatg aggggccgca agttttatca gtgatggagt tggccactcc ctctctgcgc   4800
gctcgctcgc tcactgaggc cgggcgacca aaggtcgccc gacgcccggg ctttgcccgg   4860
gcggcctcag tgagcgagcg agcgcgccag ctgcattaat gaatcggcca acgcgcgggg   4920
agaggcggtt tgcgtattgg gcgctcttcc gcttcctcgc tcactgactc gctgcgctcg   4980
gtcgttcggc tgcggcgagc ggtatcagct cactcaaagg cggtaatacg gttatccaca   5040
gaatcagggg ataacgcagg aaagaacatg tgagcaaaag gccagcaaaa ggccaggaac   5100
cgtaaaaagg ccgcgttgct ggcgtttttc cataggctcc gcccccctga cgagcatcac   5160
aaaaatcgac gctcaagtca gaggtggcga aacccgacag gactataaag ataccaggcg   5220
tttccccctg gaagctccct cgtgcgctct cctgttccga ccctgccgct taccggatac   5280
ctgtccgcct ttctcccttc gggaagcgtg gcgctttctc atagctcacg ctgtaggtat   5340
ctcagttcgg tgtaggtcgt tcgctccaag ctgggctgtg tgcacgaacc ccccgttcag   5400
cccgaccgct gcgccttatc cggtaactat cgtcttgagt ccaacccggt aagacacgac   5460
ttatcgccac tggcagcagc cactggtaac aggattagca gagcgaggta tgtaggcggt   5520
gctacagagt tcttgaagtg gtggcctaac tacggctaca ctagaaggac agtatttggt   5580
atctgcgctc tgctgaagcc agttaccttc ggaaaaagag ttggtagctc ttgatccggc   5640
aaacaaacca ccgctggtag cggtggtttt tttgtttgca agcagcagat tacgcgcaga   5700
aaaaaaggat ctcaagaaga tcctttgatc ttttctacgg ggtctgacgc tcagtggaac   5760
gaaaactcac gttaagggat tttggtcatg agattatcaa aaaggatctt cacctagatc   5820
cttttaaatt aaaaatgaag ttttaaatca atctaaagta tatatgagta aacttggtct   5880
gacagttacc aatgcttaat cagtgaggca cctatctcag cgatctgtct atttcgttca   5940
tccatagttg cctgactccc cgtcgtgtag ataactacga tacgggaggg cttaccatct   6000
ggccccagtg ctgcaatgat accgcgagac ccacgctcac cggctccaga tttatcagca   6060
ataaaccagc cagccggaag ggccgagcgc agaagtggtc ctgcaacttt atccgcctcc   6120
atccagtcta ttaattgttg ccgggaagct agagtaagta gttcgccagt taatagtttg   6180
cgcaacgttg ttgccattgc tacaggcatc gtggtgtcac gctcgtcgtt tggtatggct   6240
tcattcagct ccggttccca acgatcaagg cgagttacat gatcccccat gttgtgcaaa   6300
aaagcggtta gctccttcgg tcctccgatc gttgtcagaa gtaagttggc cgcagtgtta   6360
tcactcatgg ttatggcagc actgcataat tctcttactg tcatgccatc cgtaagatgc   6420
ttttctgtga ctggtgagta ctcaaccaag tcattctgag aatagtgtat gcggcgaccg   6480
agttgctctt gcccggcgtc aatacgggat aataccgcgc cacatagcag aactttaaaa   6540
```

-continued

```
gtgctcatca ttggaaaacg ttcttcgggg cgaaaactct caaggatctt accgctgttg   6600
agatccagtt cgatgtaacc cactcgtgca cccaactgat cttcagcatc ttttactttc   6660
accagcgttt ctgggtgagc aaaaacagga aggcaaaatg ccgcaaaaaa gggaataagg   6720
gcgacacgga aatgttgaat actcatactc ttcctttttc aatattattg aagcatttat   6780
cagggttatt gtctcatgag cggatacata tttgaatgta tttagaaaaa taaacaaata   6840
ggggttccgc gcacatttcc ccgaaaagtg ccacctgacg tctaagaaac cattattatc   6900
atgacattaa cctataaaaa taggcgtatc acgaggccct ttcgtctcgc gcgtttcggt   6960
gatgacggtg aaaacctctg acacatgcag ctcccggaga cggtcacagc ttgtctgtaa   7020
gcggatgccg ggagcagaca agcccgtcag ggcgcgtcag cgggtgttgg cgggtgtcgg   7080
ggctggctta actatgcggc atcagagcag attgtactga gagtgcacca tatgcggtgt   7140
gaaataccgc acagatgcgt aaggagaaaa taccgcatca ggaattccaa catccaataa   7200
atcatacagg caaggcaaag aattagcaaa attaagcaat aaagcctcag agcataaagc   7260
taaatcggtt gtaccaaaaa cattatgacc ctgtaatact tttgcgggag aagcctttat   7320
ttcaacgcaa ggataaaaat ttttagaacc ctcatatatt ttaaatgcaa tgcctgagta   7380
atgtgtaggt aaagattcaa acgggtgaga aaggccggag acagtcaaat caccatcaat   7440
atgatattca accgttctag ctgataaatt catgccggag agggtagcta tttttgagag   7500
gtctctacaa aggctatcag gtcattgcct gagagtctgg agcaaacaag agaatcg      7557
```

<210> SEQ ID NO 4
<211> LENGTH: 4072
<212> TYPE: DNA
<213> ORGANISM: Unknown
<220> FEATURE:
<223> OTHER INFORMATION: recombinant DNA

<400> SEQUENCE: 4

```
catcatcaat aatatacctt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactcgagt gttgacattg attattgact agttattaat agtaatcaat    600
tacggggtca ttagttcata gcccatatat ggagttccgc gttacataac ttacggtaaa    660
tggcccgcct ggctgaccgc ccaacgaccc ccgcccattg acgtcaataa tgacgtatgt    720
tcccatagta acgccaatag ggactttcca ttgacgtcaa tgggtggagt atttacggta    780
aactgcccac ttggcagtac atcaagtgta tcatatgcca agtacgcccc ctattgacgt    840
caatgacggt aaatggcccg cctggcatta tgcccagtac atgaccttat gggactttcc    900
tacttggcag tacatctacg tattagtcat cgctattacc atggtgatgc ggttttggca    960
gtacatcaat gggcgtggat agcggtttga ctcacgggga tttccaagtc tccaccccat   1020
```

-continued

```
tgacgtcaat gggagtttgt tttggcacca aaatcaacgg gactttccaa aatgtcgtaa   1080
caactccgcc ccattgacgc aaatgggcgg taggcgtgta cggtgggagg tctatataag   1140
cagagctcgt ttagtgaacc gtaagcttcg atcaactacg cagacaggta ccaaaacaaa   1200
tgttctcgtc acgtgggcat gaatctgatg ctgtttccct gcagacaatg cgagagaatg   1260
aatcagaatt caaatatctg cttcactcac ggacagaaag actgtttaga gtgctttccc   1320
gtgtcagaat ctcaacccgt ttctgtcgtc aaaaaggcgt atcagaaact gtgctacatt   1380
catcatatca tgggaaaggt gccagacgct tgcactgcct gcgatctggt caatgtggat   1440
ttggatgact gcatctttga acaataaatg atttaaatca ggtatggctg ccgatggtta   1500
tcttccagat tggctcgagg acactctctc tgaaggaata agacagtggt ggaagctcaa   1560
acctggccca ccaccaccaa agcccgcaga gcggcataag gacgacagca ggggtcttgt   1620
gcttcctggg tacaagtacc tcggaccctt caacggactc gacaagggag agccggtcaa   1680
cgaggcagac gccgcggccc tcgagcacga caaagcctac gaccggcagc tcgacagcgg   1740
agacaacccg tacctcaagt acaaccacgc cgacgcggag tttcaggagc gccttaaaga   1800
agatacgtct tttgggggca acctcggacg agcagtcttc caggcgaaaa agagggttct   1860
tgaacctctg ggcctggttg aggaacctgt taagacggct ccgggaaaaa agaggccggt   1920
agagcactct cctgtggagc cagactcctc ctcgggaacc ggaaaggcgg gccagcagcc   1980
tgcaagaaaa agattgaatt ttggtcagac tggagacgca gactcagtac ctgaccccca   2040
gcctctcgga cagccaccag cagccccctc tggtctggga actaatacga tggctacagg   2100
cagtggcgca ccaatggcag acaataacga gggcgccgac ggagtgggta attcctcggg   2160
aaattggcat tgcgattcca catggatggg cgacagagtc atcaccacca gcacccgaac   2220
ctgggccctg cccacctaca acaaccacct ctacaaacaa atttccagcc aatcaggagc   2280
ctcgaacgac aatcactact ttggctacag caccccttgg gggtattttg acttcaacag   2340
attccactgc cacttttcac cacgtgactg gcaaagactc atcaacaaca actggggatt   2400
ccgacccaag agactcaact tcaagctctt taacattcaa gtcaaagagg tcacgcagaa   2460
tgacggtacg acgacgattg ccaataacct taccagcacg gttcaggtgt ttactgactc   2520
ggagtaccag ctcccgtacg tcctcggctc ggcgcatcaa ggatgcctcc cgccgttccc   2580
agcagacgtc ttcatggtgc cacagtatgg atacctcacc ctgaacaacg ggagtcaggc   2640
agtaggacgc tcttcatttt actgcctgga gtactttcct tctcagatgc tgcgtaccgg   2700
aaacaacttt accttcagct acacttttga ggacgttcct ttccacagca gctacgctca   2760
cagccagagt ctggaccgtc tcatgaatcc tctcatcgac cagtacctgt attacttgag   2820
cagaacaaac actccaagtg gaaccaccac gcagtcaagg cttcagtttt ctcaggccgg   2880
agcgagtgac attcgggacc agtctaggaa ctggcttcct ggaccctgtt accgccagca   2940
gcgagtatca aagacatctg cggataacaa caacagtgaa tactcgtgga ctggagctac   3000
caagtaccac ctcaatggca gagactctct ggtgaatccg ggcccggcca tggcaagcca   3060
caaggacgat gaagaaaagt tttttcctca gagcggggtt ctcatctttg ggaagcaagg   3120
ctcagagaaa acaaatgtgg acattgaaaa ggtcatgatt acagacgaag aggaaatcag   3180
gacaaccaat cccgtggcta cggagcagta tggttctgta tctaccaacc tccagagagg   3240
caacagacaa gcagctaccg cagatgtcaa cacacaaggc gttcttccag gcatggtctg   3300
gcaggacaga gatgtgtacc ttcaggggcc catctgggca aagattccac acacggacgg   3360
acattttcac ccctctcccc tcatgggtgg attcggactt aaacaccctc ctccacagat   3420
```

```
tctcatcaag aacaccccgg tacctgcgaa tccttcgacc accttcagtg cggcaaagtt   3480

tgcttccttc atcacacagt actccacggg acaggtcagc gtggagatcg agtgggagct   3540

gcagaaggaa aacagcaaac gctggaatcc cgaaattcag tacacttcca actacaacaa   3600

gtctgttaat gtggacttta ctgtggacac taatggcgtg tattcagagc ctcgccccat   3660

tggcaccaga tacctgactc gtaatctgta attgcttgtt aatcaataaa ccgtttaatt   3720

cgtttcagtt gaactttggt ctctgcgtat ttctttctta tctagtttcc atggctactc   3780

tagaggatcc ccgggtaccg agctcgaatt ctttgtagag gttttacttg ctttaaaaaa   3840

cctcccacac ctcccoctga acctgaaaca taaaatgaat gcaattgttg ttgttaactt   3900

gtttattgca gcttataatg gttacaaata aagcaatagc atcacaaatt tcacaaataa   3960

agcatttttt tcactgcatt ctagttgtgg tttgtccaaa ctcatcaatg tatcttatca   4020

tgtctggatc atcgatccat aacttcgtat aatgtatgct atacgaagtt at           4072
```

```
<210> SEQ ID NO 5
<211> LENGTH: 27
<212> TYPE: DNA
<213> ORGANISM: Unknown
<220> FEATURE:
<223> OTHER INFORMATION: recombinant DNA

<400> SEQUENCE: 5

cccggatccg tttaattcgt ttcagtt                                         27


<210> SEQ ID NO 6
<211> LENGTH: 20
<212> TYPE: DNA
<213> ORGANISM: Unknown
<220> FEATURE:
<223> OTHER INFORMATION: recombinant DNA

<400> SEQUENCE: 6

cctcaatctg tatcttcatc                                                 20


<210> SEQ ID NO 7
<211> LENGTH: 5261
<212> TYPE: DNA
<213> ORGANISM: Unknown
<220> FEATURE:
<223> OTHER INFORMATION: recombinant DNA

<400> SEQUENCE: 7

catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagctgacg tgtagtgtat ttatacccgg    480

tgagttcctc aagaggccac tcttgagtgc cagcgagtag agttttctcc tccgagccgc    540

tccgacaccg ggactcgagt gttgacattg attattgact agttattaat agtaatcaat    600

tacggggtca ttagttcata gcccatatat ggagttccgc gttacataac ttacggtaaa    660
```

-continued

```
tggcccgcct ggctgaccgc ccaacgaccc ccgcccattg acgtcaataa tgacgtatgt    720
tcccatagta acgccaatag ggactttcca ttgacgtcaa tgggtggagt atttacggta    780
aactgcccac ttggcagtac atcaagtgta tcatatgcca agtacgcccc ctattgacgt    840
caatgacggt aaatggcccg cctggcatta tgcccagtac atgaccttat gggactttcc    900
tacttggcag tacatctacg tattagtcat cgctattacc atggtgatgc ggttttggca    960
gtacatcaat gggcgtggat agcggtttga ctcacgggga tttccaagtc tccaccccat   1020
tgacgtcaat gggagtttgt tttggcacca aaatcaacgg gactttccaa aatgtcgtaa   1080
caactccgcc ccattgacgc aaatgggcgg taggcgtgta cggtgggagg tctatataag   1140
cagagctcgt ttagtgaacc gtaagcttgc atgcctgcag gtcgactcta gaccatgggc   1200
ccaaagaaga agagaaaggt ttcgaattta ctgaccgtac accaaaattt gcctgcatta   1260
ccggtcgatg caacgagtga tgaggttcgc aagaacctga tggacatgtt cagggatcgc   1320
caggcgtttt ctgagcatac ctggaaaatg cttctgtccg tttgccggtc gtgggcggca   1380
tggtgcaagt tgaataaccg gaaatggttt cccgcagaac ctgaagatgt tcgcgattat   1440
cttctatatc ttcaggcgcg cggtctggca gtaaaaacta tccagcaaca tttgggccag   1500
ctaaacatgc ttcatcgtcg gtccgggctg ccacgaccaa gtgacagcaa tgctgtttca   1560
ctggttatgc ggcggatccg aaaagaaaac gttgatgccg gtgaacgtgc aaaacaggct   1620
ctagcgttcg aacgcactga tttcgaccag gttcgttcac tcatggaaaa tagcgatcgc   1680
tgccaggata tacgtaatct ggcatttctg gggattgctt ataacaccct gttacgtata   1740
gccgaaattg ccaggatcag ggttaaagat atctcacgta ctgacggtgg gagaatgtta   1800
atccatattg gcagaacgaa aacgctggtt agcaccgcag gtgtagagaa ggcacttagc   1860
ctgggggtaa ctaaactggt cgagcgatgg atttccgtct ctggtgtagc tgatgatccg   1920
aataactacc tgttttgccg ggtcagaaaa aatggtgttg ccgcgccatc tgccaccagc   1980
cagctatcaa ctcgcgccct ggaagggatt tttgaagcaa ctcatcgatt gatttacggc   2040
gctaaggatg actctggtca gagatacctg gcctggtctg gacacagtgc ccgtgtcgga   2100
gccgcgcgag atatggcccg cgctggagtt tcaataccgg agatcatgca agctggtggc   2160
tggaccaatg taaatattgt catgaactat atccgtaacc tggatagtga aacaggggca   2220
atggtgcgcc tgctggaaga tggcgattag gaattctttg tagaggtttt acttgcttta   2280
aaaaacctcc cacacctccc cctgaacctg aaacataaaa tgaatgcaat tgttgttgtt   2340
aacttgttta ttgcagctta taatggttac aaataaagca atagcatcac aaatttcaca   2400
aataaagcat ttttttcact gcattctagt tgtggtttgt ccaaactcat caatgtatct   2460
tatcatgtct ggatcatcga tccataactt cgtataatgt atgctatacg aagttatcca   2520
gatctggttc tatagtgtca cctaaatcgt atgtgtatga tacataaggt tatgtattaa   2580
ttgtagccgc gttctaacga caatatgtcc atagggcccc tacgtcaccc gccccgttcc   2640
cacgccccgc gccacgtcac aaactccacc ccctcattat catattggct tcaatccaaa   2700
ataaggtata ttattgatga tggccgcagc ggcccctggc gtaatagcga agaggcccgc   2760
accgatcgcc cttcccaaca gttgcgcagc ctgaatggcg aatgggacgc gccctgtagc   2820
ggcgcattaa gcgcggcggg tgtggtggtt acgcgcagcg tgaccgctac acttgccagc   2880
gccctagcgc ccgctccttt cgctttcttc ccttcctttc tcgccacgtt cgccggcttt   2940
ccccgtcaag ctctaaatcg gggctccct ttagggttcc gatttagtgc tttacggcac   3000
ctcgacccca aaaaacttga ttagggtgat ggttcacgta gtgggccatc gccctgatag   3060
```

-continued

```
acggtttttc gccctttgac gttggagtcc acgttcttta atagtggact cttgttccaa   3120

actggaacaa cactcaaccc tatctcggtc tattcttttg atttataagg gattttgccg   3180

atttcggcct attggttaaa aaatgagctg atttaacaaa aatttaacgc gaattttaac   3240

aaaatattaa cgcttacaat ttaggtggca cttttcgggg aaatgtgcgc ggaaccccta   3300

tttgtttatt tttctaaata cattcaaata tgtatccgct catgagacaa taaccctgat   3360

aaatgcttca ataatattga aaaaggaaga gtatgagtat tcaacatttc cgtgtcgccc   3420

ttattccctt ttttgcggca ttttgccttc ctgtttttgc tcacccagaa acgctggtga   3480

aagtaaaaga tgctgaagat cagttgggtg cacgagtggg ttacatcgaa ctggatctca   3540

acagcggtaa gatccttgag agttttcgcc ccgaagaacg ttttccaatg atgagcactt   3600

ttaaagttct gctatgtggc gcggtattat cccgtattga cgccgggcaa gagcaactcg   3660

gtcgccgcat acactattct cagaatgact tggttgagta ctcaccagtc acagaaaagc   3720

atcttacgga tggcatgaca gtaagagaat tatgcagtgc tgccataacc atgagtgata   3780

acactgcggc caacttactt ctgacaacga tcggaggacc gaaggagcta accgcttttt   3840

tgcacaacat gggggatcat gtaactcgcc ttgatcgttg ggaaccggag ctgaatgaag   3900

ccataccaaa cgacgagcgt gacaccacga tgcctgtagc aatggcaaca acgttgcgca   3960

aactattaac tggcgaacta cttactctag cttcccggca acaattaata gactggatgg   4020

aggcggataa agttgcagga ccacttctgc gctcggccct tccggctggc tggtttattg   4080

ctgataaatc tggagccggt gagcgtgggt ctcgcggtat cattgcagca ctggggccag   4140

atggtaagcc ctcccgtatc gtagttatct acacgacggg gagtcaggca actatggatg   4200

aacgaaatag acagatcgct gagataggtg cctcactgat taagcattgg taactgtcag   4260

accaagttta ctcatatata ctttagattg atttaaaact tcatttttaa tttaaaagga   4320

tctaggtgaa gatccttttt gataatctca tgaccaaaat cccttaacgt gagttttcgt   4380

tccactgagc gtcagacccc gtagaaaaga tcaaaggatc ttcttgagat cctttttttc   4440

tgcgcgtaat ctgctgcttg caaacaaaaa aaccaccgct accagcggtg gtttgtttgc   4500

cggatcaaga gctaccaact ctttttccga aggtaactgg cttcagcaga gcgcagatac   4560

caaatactgt ccttctagtg tagccgtagt taggccacca cttcaagaac tctgtagcac   4620

cgcctacata cctcgctctg ctaatcctgt taccagtggc tgctgccagt ggcgataagt   4680

cgtgtcttac cgggttggac tcaagacgat agttaccgga taaggcgcag cggtcgggct   4740

gaacgggggg ttcgtgcaca cagcccagct tggagcgaac gacctacacc gaactgagat   4800

acctacagcg tgagctatga gaaagcgcca cgcttcccga agggagaaag gcggacaggt   4860

atccggtaag cggcagggtc ggaacaggag agcgcacgag ggagcttcca gggggaaacg   4920

cctggtatct ttatagtcct gtcgggtttc gccacctctg acttgagcgt cgatttttgt   4980

gatgctcgtc aggggggcgg agcctatgga aaaacgccag caacgcggcc tttttacggt   5040

tcctggcctt ttgctggcct tttgctcaca tgttctttcc tgcgttatcc cctgattctg   5100

tggataaccg tattaccgcc tttgagtgag ctgataccgc tcgccgcagc cgaacgaccg   5160

agcgcagcga gtcagtgagc gaggaagcgg aagagcgccc aatacgcaaa ccgcctctcc   5220

ccgcgcgttg gccgattcat taatgcaggg gccgctgcgg c                       5261
```

<210> SEQ ID NO 8
<211> LENGTH: 26
<212> TYPE: DNA

-continued

```
<213> ORGANISM: Unknown
<220> FEATURE:
<223> OTHER INFORMATION: recombinant DNA

<400> SEQUENCE: 8

cccggatccc ttctcaaatt gcacaa                                          26
```

RECOMBINANT AAV PACKAGING SYSTEMS

CROSS REFERENCE TO RELATED APPLICATIONS

This application claims the benefit of U.S. Provisional Application No. 60/178,536, filed Jan. 26, 2000, which is herein incorporated by reference in its entirety.

REFERENCE TO SEQUENCE LISTING, TABLES OR COMPUTER PROGRAM LISTING

A Sequence Listing has also been included herein in accordance with the provisions of 37 C.F.R. §1.821 et seq. To the extent any discrepancy exists between the Specification Figures and the Sequence Listing, the Specification or Figures should be considered to be the primary document.

TECHNICAL FIELD

The present invention relates generally to compositions and methods for producing recombinant adeno-associated virus (rAAV) vectors. More specifically, the present invention relates to packaging cell lines and methods for making and using them. Moreover, the rAAV packaging cell lines of the present invention are used to produce high-titer rAAV, that is free of replication-competent AAV and that are suitable for a wide range of applications including ex vivo and in vivo gene therapy as well as in vitro recombinant protein production.

BACKGROUND OF THE INVENTION

Adeno-associated virus (AAV) is a ubiquitous single stranded DNA parvovirus capable of infecting a wide range of cell types from a variety of different species. Under normal physiological conditions, AAV enters the host cell where it is transported to the cell nucleus. Once inside the cell nucleus, the viral capsid is removed and the viral DNA is stably integrated into the host chromosome. After integration, AAV remains dormant and is generally incapable of self-replication. However, AAV replication can be induce when the cell containing the latent AAV DNA is co-infected with either an adenovirus or a member of the hepresviradae, including herpes simplex virus (HSV), cytomegalovirus (CMV), Epstein Barr virus (EBV) or Vaccina Virus and pseudorabies virus (Berns, K. I. Parvoviridae: The Viruses and Their Replication. In: Fields, B. N. ed. *Virology*. Philadelphia. Lippincott-Raven 1996 Third Edition Vol. 2 2181–2192.) These so-called "helper viruses" provide AAV the necessary helper functions required to rescue and activate the AAV genome and initiate transcription.

Gene therapy, which provides a method for altering the genetic repertoire of cells for a therapeutic benefit has shown promise for treating or preventing a number of diseases. For example, such therapies are now being tested in clinical trials for a range of hereditary (e.g., ADA deficiency, familial hypercholesterolemia, and cystic fibrosis) and acquired (e.g., cancer, viral infection) diseases (Crystal, *Science* 270:404–410, 1995). Furthermore, gene therapy has shown promise for a variety of vaccine applications.

Many different types of vectors, principally viral vectors, can be utilized for a variety of gene therapy applications, including for example, viral vectors derived from retroviruses, adenoviruses, poxviruses, herpes viruses, and adeno-associated viruses (see Jolly, *Cancer Gene Therapy* 1:51–64, 1994). One difficulty, however, for present viral-based vectors (and for adeno-associated viral vectors in particular), is that large quantities of viral particles are difficult to produce in a cost-efficient commercial setting.

Data from animal experiments suggest that recombinant AAV (rAAV) may be useful in delivering genes to treat a number of diseases including hemophilia A and B, Gauche's disease, Parkinson's disease and retinitis pigmentosa. Despite this experimental success, there is only one human trial in progress with an AAV vector compared to hundreds already conducted with retrovirus or adenovirus vectors. One reason for this disparity is that there has been less development of AAV based vectors, and this in turn reflects the amount of attention that the basic biology each virus group has received. A second and more practical reason is the difficulty in obtaining the amount of rAAV needed for clinical trials, let alone a medical product. The current trial uses transient transfection to manufacture material, a procedure suited to the lab bench but not particularly friendly to a manufacturing suite. As an alternative, cell line technology is more easily scaled and far less likely to generate replication competent virus.

So far the approach for making recombinant AAV producer cell lines employs the techniques used for retrovirus vectors—remove the origins and packaging sequences from the viral genes and select for stable integration by co-transfecting the remainder with a resistance marker. For AAV, the origins and packaging sequence are found in the inverted terminal repeats (ITR's). This approach has proven far less successful with AAV than retrovirus. Of the resulting clones, only a few contain intact AAV genomes, and even fewer are capable of making vector particles. Out of these, only an extremely rare clone makes a useful amount of vector (Gao, G. P et al. High-Titer Adenoassociated Viral Vectors from a Rep/Cap Cell Line and Hybrid Shuttle Virus. Human Gene Therapy. 9:2353–62).

AAV efficiently establishes latent infections in the absence of helper virus (Berns, K. I. et al. Adeno-associated virus Latent Infections. In: MayBWJ et al. eds. *Virus Persistence*. Cambridge: Cambridge University press. 1982; 249.). This natural pathway is tantalizing to anyone trying to create new rAAV packaging technology since such latently infected cells appear to be stable for many generations, and in contrast to transfected cells, virtually all the latently infected cells can be activated to make up to $10^6$ particles of AAV(Berns, K. I. et al. Adeno-associated virus Latent Infections. In: May BWJ et al. eds. *Virus Persistence*. Cambridge: Cambridge University press. 1982; 249). Clearly the differences between wild type AAV and current producer cell lines are critical. One important difference is that AAV integrates into a limited number of specific sites in human DNA as opposed to random integration by transfection and selection (Cheung A-M et al. 1980. J. Virol. 33:739). Specific integration appears to require three components: AAV ITR's containing rep-binding sites, chromosomal DNA with rep binding sites, and rep protein (Chapman MS et al. 1993. Virol. 194:491). The silent state of latent virus and its efficient activation by helper virus maybe properties of the chromosomal location of the latent viral genomes. However, data indicates that at least for activation of AAV expression the ITR's are also a critical component (Im, DS et al. 1989. J. Virol. 63:3095).

The present invention discloses novel compositions and methods for generating recombinant AAV vectors, and further provides other related advantages.

BRIEF SUMMARY OF THE INVENTION

Briefly stated, the present invention provides compositions and methods for generating recombinant AAV vectors.

Specifically, the present invention provides pharmaceutical preparations of rAAV suitable for use in ex vivo and in vivo gene therapy as well as in vitro recombinant antigen production. Generally, the present invention provides high-titer rAAV suspensions that are produced in eukaryotic cells. The rAAV suspensions are free from replication-competent rAAV, wild type AAV. This is achieved by infecting a suitable host eukaryotic cell using a first recombinant AAV vector having a first site specific recombination locus inserted between the 5' inverted terminal repeat (ITR) sequence and the rep gene and a second site specific recombination locus inserted between the 3' ITR and the cap gene.

Next, the host cell infected with the first rAAV is infected with a second rAAV having a gene of interest substituted for the rep and cap regions of the AAV genome. The two rAAVs may be used to infect the host cell simultaneously, or sequentially. Recombinant AAV infectious particle production and packaging is induced by infecting the host cell containing the first and second rAAV genomes using a wild type helper virus and two helper virus recombinant variants. The first recombinant variant helper virus expresses a recombinase gene (Cre) and the second recombinant variant helper virus has a site-specific recombination locus genome insert. It is understood that the helper virus infection of the eukaryotic host cell may proceed in any order, or may be performed simultaneously.

In another embodiment of the present invention rAAV production and packaging is induced using a wild type helper virus and a single recombinant helper virus having both a site specific recombination locus and a gene encoding for Cre recombinase.

It yet another embodiment of the present invention the recombinant helper virus has a site specific recombination locus, a Cre recombinase gene and all necessary helper genes. In this embodiment only a single helper virus is necessary to induce the production of replication incompetent recombinant AAV particles.

Within one aspect of the present invention recombinant adeno-associated virus are provided comprising 5' AAV ITR, a first site specific recombination locus, rep and cap genes, and a second site specific recombination locus which is capable of recombining with the first site specific recombination locus. Within preferred embodiments, the virus further comprise a 3' AAV ITR. Representative site-specific recombination loci are loxP and FRT. Also provided are plasmids that comprise a DNA sequence of the aforementioned viruses. In another embodiment of the present invention a recombinant retrovirus is provided having an 5'LTR, a packaging signal, an AAV rep region, an AAV cap region and a 5' LTR. Other recombinant retrovirus variations are also possible which include, but are not limited to, inverting the AAV rep and cap genes relative to each other, adding selection markers and truncating the LTRs.

Within other embodiments of the invention, methods are provided for producing recombinant AAV vector particles; comprising the steps of (a) introducing into a host cell (i) pfloxAAV, (ii) a recombinant AAV vector encoding plasmid, and (iii) a plasmid encoding a member of the herpesviridae (e.g., herpesvirus or cytomegalovirus), Epstein-Barr virus, or adenovirus, which supplies necessary helper functions, or, a virus or viral vector which encodes such functions, in order to produce flox AAV particles and recombinant AAV particles; and (b) introducing into a second host cell (i) the recombinant AAV particles and flox AAV particles of (a), (ii) a vector which directs the expression of Cre, and (iii) a vector which directs the expression of herpesvirus, CMV, or adenovirus helper functions, such that said recombinant AAV vector particles are produced. Within further embodiments, a vector which directs the expression of cap may also be introduced into the second host cell. Within certain embodiments, the second host cell does not produce E1A. Further, as should be readily evident a variety of vectors or particles other than pflox AAV or flox AAV particles may be utilized in the context of the present invention, including for example, vectors or particles that have at least one site specific recombination locus as discussed above.

Within further embodiments of the invention plasmids are provided which encode a member of the herpesviridae (e.g., herpesvirus or cytomegalovirus), vaccinia virus, Epstein-Barr virus, or adenovirus, which supplies necessary helper functions (in order to produce flox AAV particles and recombinant AAV particles), and which also have a pair of site specific recombination locus (e.g., loxP sequences).

Within other aspects of the present invention, host cells are provided which comprise an integrated DNA sequence of the recombinant adeno-associated virus described herein. Within further embodiments, the host cells further comprise a recombinant AAV vector.

Within further aspects of the present invention, circular DNA is provided, comprising rep and cap genes, wherein the circular DNA does not have an origin of replication. Preferably, the circular DNA does not have an origin of replication of either bacterial or eukaryotic origin.

Within yet other aspects of the present invention, recombinant adeno-associated cap (−) viruses are provided, comprising, 5' AAV ITR, a first site specific recombination locus, the rep genes, a second site specific recombination locus which is capable of recombining with said first site specific recombination locus, and a 3' AAV ITR, with the proviso that the recombinant adeno-associated cap (−) virus does not contain any functional cap genes. Within further embodiments, the recombinant adeno-associated cap(−) virus further comprises poly(A) sequence. Within related aspects, plasmids are provided which comprise a DNA sequence of such recombinant adeno-associated viruses.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIG. 5 is a table which shows stable cell line vector production.

FIG. 6 is a table which shows the difference between AAV and flox AAV plasmids in vector production.

DETAILED DESCRIPTION OF THE INVENTION

Definitions

Figure 1:
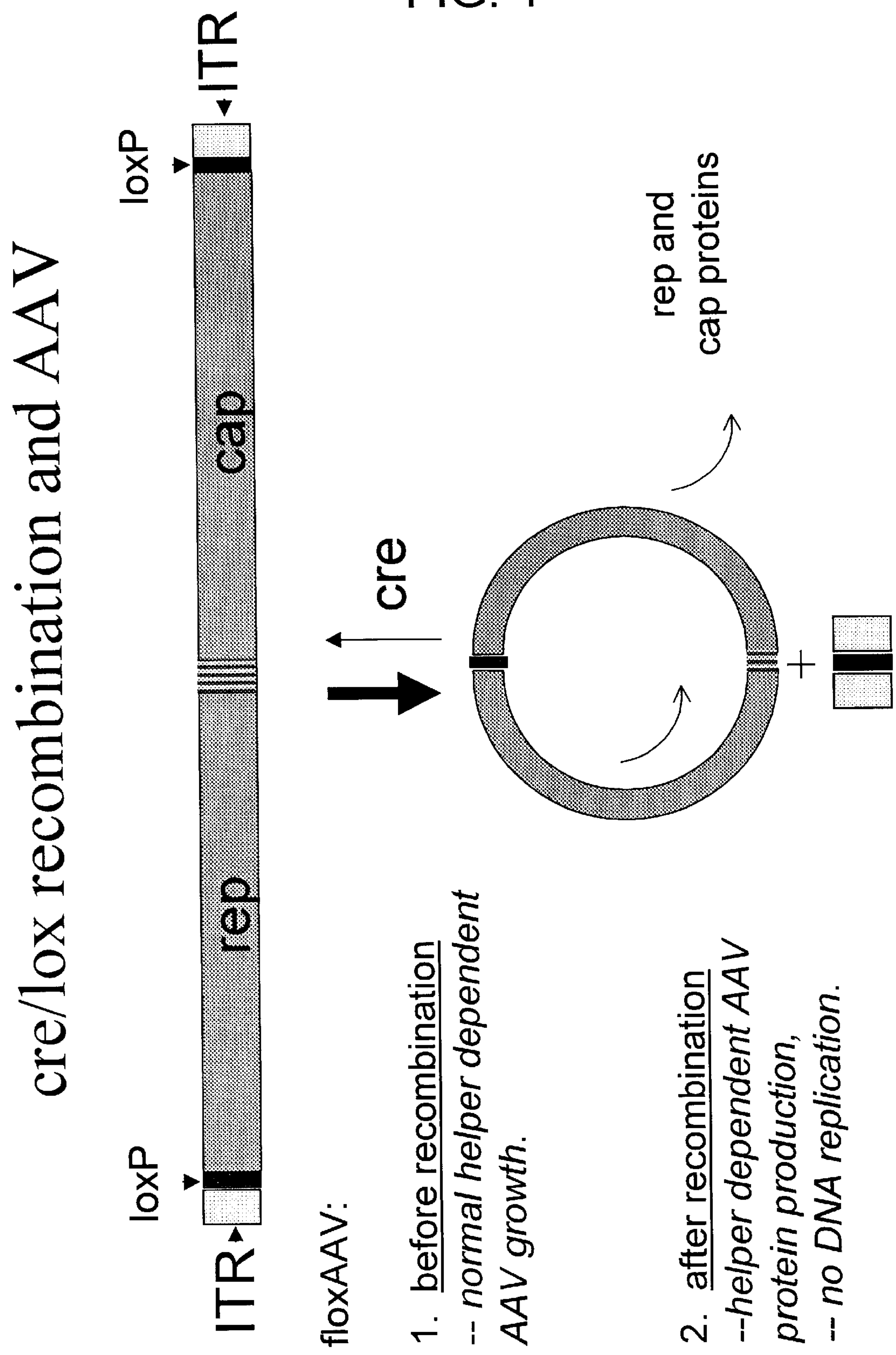
FIG. 1 is a schematic illustration which shows one representative embodiment of a flox AAV vector, which circularizes upon addition of Cre.

Prior to setting forth the invention, it may be helpful to an understanding thereof to first set forth definitions of certain terms that will be used hereinafter.

"Site specific recombination locus" refers to specific nucleic acid sequences which are the targets of a "recombinase" which catalyzes strand exchange between two sites. Representative examples of site-specific recombination locus suitable for use within the present invention include lox P and FRT sites. Representative examples of recombinases include Cre, which can be utilized for lox P sites, and FLP, to be used with FRT sites.

"Recombinant adeno-associated virus vector" or "rAAV vector" refers to a gene delivery vector based upon an adeno-associated virus. The rAAV vectors, should contain 5' and 3' adeno-associated virus inverted terminal repeats (ITRs), and a transgene or gene of interest operatively linked to sequences which regulate its expression in a target cell. Within certain embodiments, the transgene may be operably linked to a heterologous promoter (such as CMV), or, an inducible promoter (such as tet). In addition, the rAAV vector may have a polyadenylation sequence.

Adeno-associated virus (AAV) is a single stranded DNA virus belonging to the parvoviradae—more specifically AAV is a dependovirus. Like all members of the parvoviradae AAV is a non-enveloped virus having a viral capsid composed of three viral proteins, VP1, VP2 and VP3. The smallest of the three capsid proteins, VP3 comprises approximately 90 per cent of the viral capsid. The remaining 10 percent is composed of nearly equal amounts of VP1 and VP2.

Adeno-associated virus possess a 4.7 kb genome that is generally composed of two inverted terminal repeats (ITR) of 145 base pairs (bp) each that flank a large non-repeating open reading frame (ORF). The AAV ITRs contain sequences required in cis for packaging, genome integration and subsequent AAV DNA rescue and replication (McLaughlin, S. K. 1988. J. Virol. 62:1963–1973). The internal non-repeating region flanked by AAV ITRs is divided into two discrete gene regions that regulate viral replication and encode for structural proteins. The left region nearest the 5' ITR is referred to as the rep region and encodes for at least four viral proteins that are involved with AAV gene expression and repression. The rep proteins are named for their respective molecular weights and hence referred to as REP40, REP52, REP68 and REP78. A p5 promoter regulates the transcription of REP 68 and 78 whereas REPs 40 and 52 are regulated via the p19 promoter. The two larger rep proteins, REP 68 and REP 78, are involved in site-specific integration in the host genome and negatively regulate AAV gene expression and DNA replication in the absence of a helper virus. However, in the presence of a helper virus, these same two large rep proteins act as transactivators of AAV gene expression and are essential for DNA replication and rescue from the viral genome. The right internal gene region nearest the 3' ITR is referred to as cap and encodes for the three AAV capsid proteins VP1, VP2, and VP3. The smallest cap protein, VP3 is the most abundant and accounts for more that 90% of AAV's viral capsid.

Adeno-associated viruses enter a host cell and migrate to the nucleus where they are uncoated exposing their single stranded DNA. After AAV enters the host cell nucleus it integrates into the host DNA (at chromosome 19 in humans) and is converted to double stranded DNA by host polymerase enzymes. Generally, multiple copies of the AAV genome are integrated head to tail at the same integration site. The integrated AAV DNA is a latent provirus that is stably integrated into the host genome and does not self-replicate or form progeny AAV except in the presence of a helper virus.

Helper viruses are viruses that can rescue the latent AAV genome from the host chromosome and initiate progeny AAV replication. Helper viruses include adenoviruses, herpesviradae, vaccinia virus and pseudorabies. Adeno-associated virus helper function has been extensively studied using adenovirus as the primary model. In adenovirus (Ad) systems the Ad early function serves as helper functions for AAV, no Ad late AAV dependent helper functions have been identified. Adenovirus early region 1A (E1A), E1B, E2A, E4 and VA are required for AAV replication. Adenovirus E1A transactivates the p5 and p19 promoters of AAV which in turn initiate transcription of rep proteins. These rep proteins, specifically at least one p5 REP protein, induce coordinated mRNA synthesis by the remaining AAV promoters resulting in a 50-fold, or greater, production of AAV mRNA (Muzyczka, N, 1992. Current Topics in Micro. And Immun. Vol. 158 97–129). Adenovirus E1B encodes for a 55 kD transforming protein, and together with the 34 kD E-4-coded protein stabilize AAV mRNA and/or facilitate its transport to the cytoplasm. Capsid p40 mRNA translation is regulated by E2A, a DNA binding protein, and the adenovirus VA gene. Together, the adenovirus E1A, E1B, E2A, E4 and VA genes products help induce and maximize the expression of AAV-gene products, but are not directly involved in AAV DNA replication (Yalkinglu, A. O., 1988. Cancer Res. 48:3123–3125).

As previously discussed, AAV is a ubiquitous animal virus that has a remarkably diverse host range. Furthermore, AAV has never been associated with diseases in man or lower animals (Ostrove, et al. 1987. Virology 113:521–533). Therefore, AAV is considered an ideal gene therapy vector candidate. Recombinant AAV was first produced in 1982 when Samulski cloned intact duplex AAV DNA in the bacterial plasmid pBR322. Samulski then transfected human cells using the AAV pBR322 plasmid and demonstrated that AAV genome could be rescued from the transfected cells following adenovirus 5 infection (Samulski, et al 1982. Proc. Natl. Acad. Sci. U.S.A. 79:2077–2081). Subsequently, numerous other researchers have developed AAV vector systems suitable for expressing genes using eukaryotic cells. For example, U.S. Pat. No. (USPN) 4,797,369 ("the '369 patent") issued to Carter et al. on Jan. 10, 1989 discloses vectors comprising part of AAV DNA contained in a plasmid and capable of being packaged into AAV particles. The resulting AAV particles function as vectors for stable integration and expression of a gene in eukaryotic cells when under the control of an AAV transcription promoter. Carter was able to successfully produce high tittered rAAV particles in HELA cells that could be used to transform fresh cells. However, Carter's methods disclosed in the '369 patent resulted in significant wild type recombinant AAV contamination. Moreover, Carter commented " . . . it is still not possible to completely avoid generation of wild type recombinant."

In U.S. Pat. No. 5,139,941 issued Aug. 18, 1992 ("the '941 patent"), Myzyczka et al. disclose a hybrid gene vector suitable for inducing foreign DNA into mammalian cells comprising the foreign DNA ligated to an AAV genome. Specifically, the DNA was ligated into the AAV genome in place of the rep and/or cap region and then cloned into a prokaryotic vectored plasmid. The resulting AAV plasmid was used to transfect mammalian cells along with a second plasmid containing all of the AAV coding regions in addition to a 1.1 kilo base (kb) fragment of bacteriophage lambda. The transfected cells were then infected with helper virus (adenovirus type 2) resulting in production of recombinant AAV. However, this method also resulted in the production of replication competent wild type AAV.

Samulski et al. disclose a system for replication and encapsidation of recombinant DNA fragments into AAV virus particles in U.S. Pat. No. 5,478,745 ("the '745 patent). Specifically, the '745 patent discloses a novel 165 bp fragment of DNA containing AAV ITR sequences. Other vector systems for the generation of adeno-associated virus particles are disclosed in U.S. Pat. No. 5,693,531 issued to Chiorini et al. Dec. 2, 1997 which discloses an AAV vector having an inducible origin of replication derived from SV 40 virus. Yet another recombinant AAV vector system is disclosed in U.S. Pat. No. 5,436,146 issued to Shenk et al. Jul. 25, 1995.

Additional AAV vector production methods and AAV vector compositions can be found in U.S. Pat. No. 5,658,785 issued to Johnson on Aug. 19, 1997, U.S. Pat. No. 5,858,775 also issued to Johnson on Jan. 1, 1999, U.S. Pat. No. 5,589,377 to Lebkowski et al. issued Dec. 31 1996, and U.S. Pat. No. 5,622,856 issued to Natsoulis Apr. 22, 1997. International application numbers WO 98/09524 entitled "Methods and Compositions for Liver Specific Delivery of Therapeutic Molecules using Recombinant AAV Vectors" and WO 99/20779 entitled "Amplifiable Adeno-associated Virus (AAV) packaging cassettes for the Production of Recombinant AAV Vectors" provide further examples.

The afore cited patents and publications, all of which are hereby incorporated in their entirety by reference, serve to illustrate the intense interest level that has recently been focused on AAV as a potential heterologous gene delivery system. However, the cited patents and publications do not describe large scale AAV vector production systems that produce high-titer, wild type replication competent virus-free preparations suitable for commercial applications. Therefore, the present inventor have developed, and disclose herein, novel methods and compositions amenable to large scale, good manufacturing practices (GMP) manufacturing environments that provide high-titer AAV vectors preparations free from replication competent AAV.

The present invention provides a highly flexible, and thus manufacturing friendly, system for the production of rAAV vector particles. In addition to rAAV vector particles, the present invention also provides stable cell lines and recombinant viruses suitable for use with the present invention. In one embodiment the present invention eukaryotic cells that stably carry a first recombinant AAV genome having site-specific recombination loci inserted to the AAV genome are provided. These site-specific recombination loci flank the rep/cap region of the AAV genome (for convenience, and not intended as a limitation, a eukaryotic cell stably carrying this recombinant AAV genome will be referred to hereinafter as an AAV vector particle packaging cell). When exposed to a recombinase such as Cre, the AAV rep/cap region is excised and forms an inactive extrachromosomal piece of circular DNA. This aspect of the present invention, which will be discussed in greater detail below, is particularly useful in providing AAV structural genes necessary for vector particle packaging. It is also understood that the first rAAV genome may be delivered as two separate rAAV genomes. For example, one rAAV genome may be composed of a 5' AAV ITR, a first site specific recombination locus, an AAV rep gene sequence, a second site specific recombination locus and a 3' AAV ITR. The other rAAV genome may be composed of 5' AAV ITR, a first site specific recombination locus, an AAV cap gene sequence, a second site specific recombination locus and a 3' AAV ITR. In this embodiment both rAAV genomes would be required to provide the full complement of rAAV structural genes.

In another aspect of the present invention the AAV vector particle-packaging cell also stably carries a second recombinant AAV genome consisting of AAV ITRs that flank a heterologous gene of interest. Suitable heterologous genes of interest include, but are not limited to DNA sequences encoding tumor necrosis factor (TNF), such as TNF-alpha, interferons such as Interferon-alpha, Interferon-beta, and Interferon-gamma, interleukins such as IL-1, II -1beta, and Interleukins 2 through 14, GM-CSF adenosine deaminase (ADA), cellular growth factors, such as lymphokines, soluble CD4, Factor VIII, Factor IX, T-cell receptors, the LDL receptor, ApoE, ApoC, alpha-1antitrypsin (alpha-1AT), ornithine transcarbamylase (OTC), CFTR, insulin, Fc receptors for antigen-binding domains of antibodies, and anti-sense sequences which inhibit viral replication, such as anti-sense sequences which inhibit replication of hepatitis B or hepatitis C virus.

The heterologous gene of interest of the present invention may also include a suitable promoter including, but not limited to adeno-associated virus promoters, adenoviral promoters, such as the adenoviral major late promoter, or heterologous promoters, such as the cytomegalovirus (CMV) promoter, the Rous Sarcoma Virus promoter, the respiratory syncytial virus (RSV) promoter, and/or inducible promoters, such as, the metallothionein promoter, the MMTV promoter and heat shock promoters.

The recombinant AAV genomes used to construct the AAV particle packaging cell of the present invention may be introduced in the eukaryotic cell using any one of a number of means known to those having ordinary skill in the art. In one embodiment of the present invention the eukaryotic cell is transfected with a plasmid using techniques known to those skilled in the art. The plasmid containing the rAAV genome may then be inserted in the eukaryotic cell using standard techniques including, but not limited to incubating cells with DNA that has been co-precipitated with either calcium phosphate or DEAE-dextran or electroporation using purified transfecting DNA.

In another embodiment of the present invention the eukaryotic cells are infected with viral vectors containing the recombinant AAV genomes. Infectious viruses containing the recombinant AAV genes include, but are not limited to rAAV and recombinant retroviruses. Examples of recombinant AAV vectors and recombinant retrovirus vectors are provided below.

Any number of different eukaryotic cells may be used as the AAV particle-packaging cell of the present invention. Adeno-associated virus has a wide host range and can infect a wide variety of cell types, moreover, when transfecting techniques are used to deliver the rAAV genomes of the present invention, an equally broad array of cell types can be used. For example, mammalian cells such as, but not limited to Hela cells, Hep-2 cells, CHO cells, human fibroblasts cells including WI-38 and MRC-5 cells, monkey kidney cells including Vero cells, BGMK and LLC-MK cells. Generally, any cell that can be easily cultured in large scale, that is endogenous virus-free and helper virus permissive is a suitable host cell for the present invention.

After a host cell has been provided with the AAV structural genes and the gene of interest, the AAV particle-packaging cell can be induced to produce infectious, non-replicating rAAV particles containing a gene of interest. Induction requires the rescue and transcription of the gene of interest and the AAV structural genes previously introduced into the AAV particle-packaging cell of the present invention. Rescue is accomplished when the AAV particle-packaging cell is infected with a helper virus, such as but not limited adenovirus. However, the use of a helper virus alone would cause the entire AAV genome containing the structural gene to be rescued, copied, transcribed, translated and packaged resulting in infectious, replication competent AAV. To avoid this result, the present inventor originally sought to induce expression of just the AAV structural genes, rep and cap, without rescuing the entire genome. This is where the site specific recombination loci inserted into the AAV gene as described above comes into play.

Figure 3:
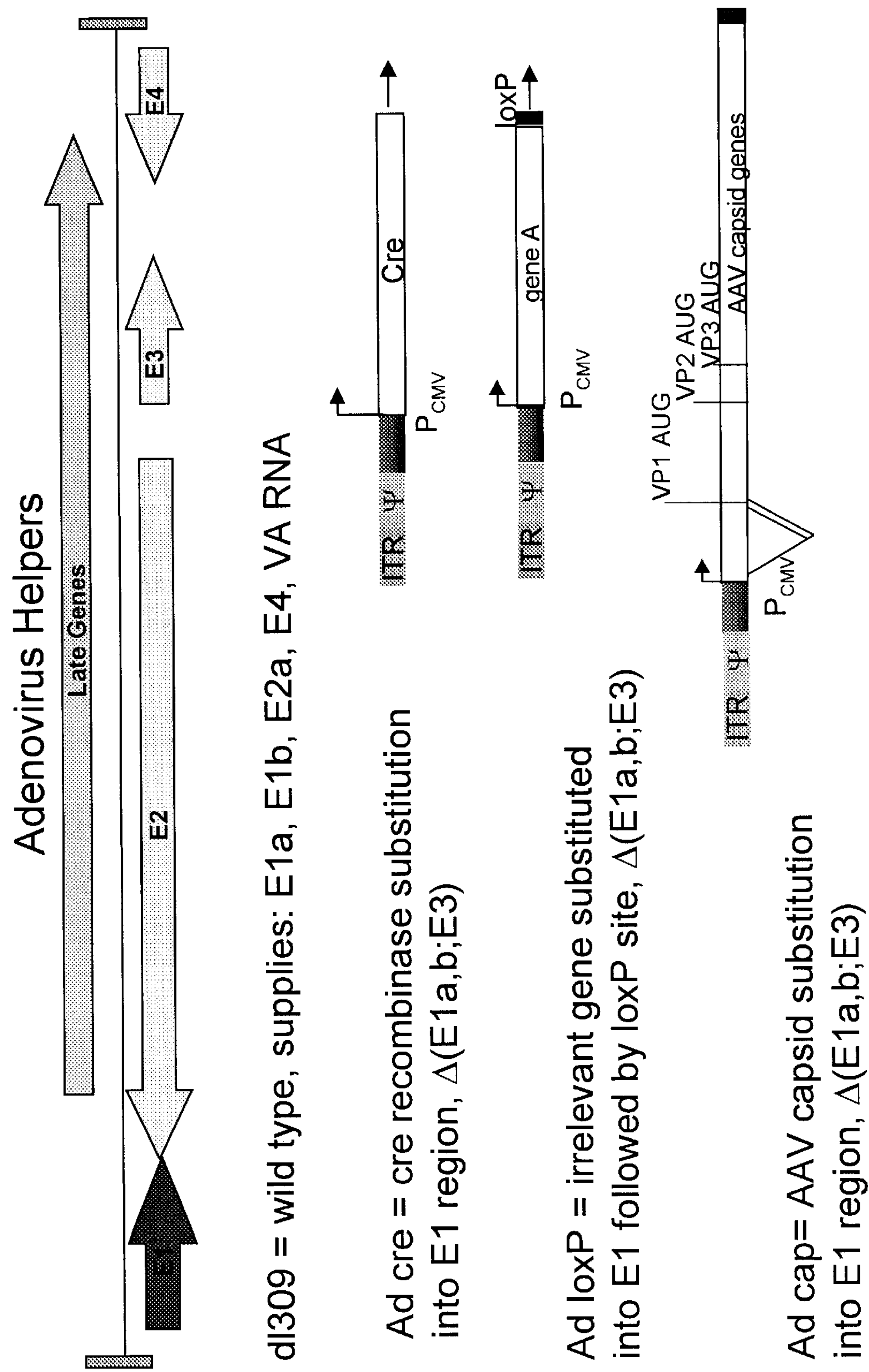
FIG. 3 schematically illustrates several adenovirus helpers.
Figure 4:
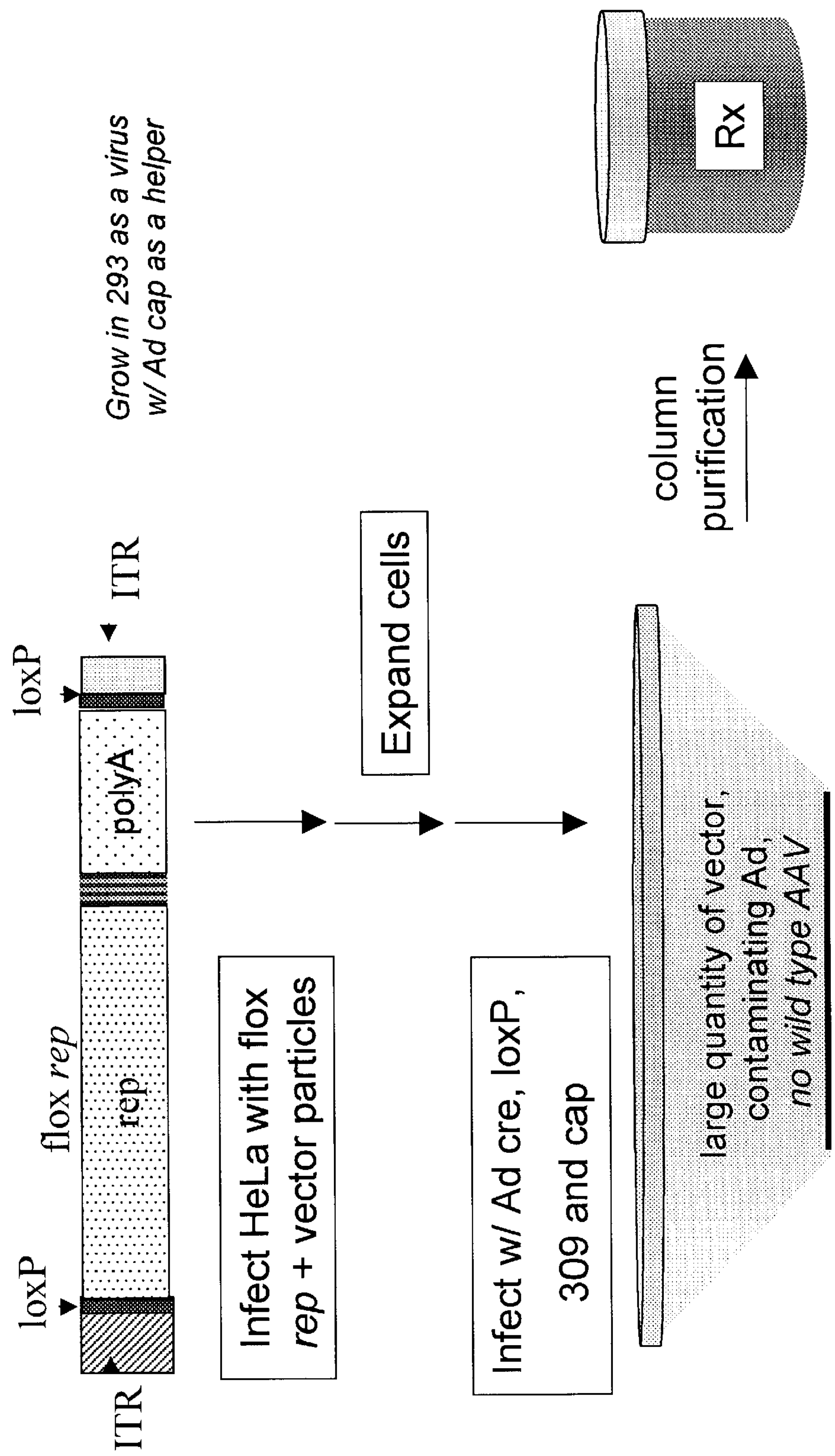
FIG. 4 schematically illustrates a rep gene which has been split from a cap gene, and which (along with Ad Cre loxP and Ad cap) can be utilized to produce recombinant AAV.

In one embodiment of the present invention the site-specific recombination loci are a loxP (locus of crossing over) sites. LoxP is a phage derived recombination site responsive to the bacterial recombinase, "Cre." When two loxP sites situated on a linear strand of DNA are exposed to Cre, the intervening nucleic acid sequence is excised and forms a circular extra-chromosomal DNA molecule as depicted in FIG. 1. Originally, the present inventor theorized that by excising just the rep/cap region of the first rAAV genome from the host chromosome replication competent AAV particle could not form because the essential ITR gene sequences would be absent. Therefore, the present inventor designed an induction system using a wild type adenovirus (adenovirus strain 309) and a recombinant adenovirus (Ad Cre) lacking the E1 region and expressing Cre in its place (see FIG. 3). It was further theorized that the fast acting Cre would excise the rep/cap region from the host chromosome as the wild type adenovirus early gene products induced expression of the the rep and cap genes. The rep and cap proteins would in turn rescue, replicate and package the rAAV genome containing a gene of interest into functional AAV capsids.

Figure 2:
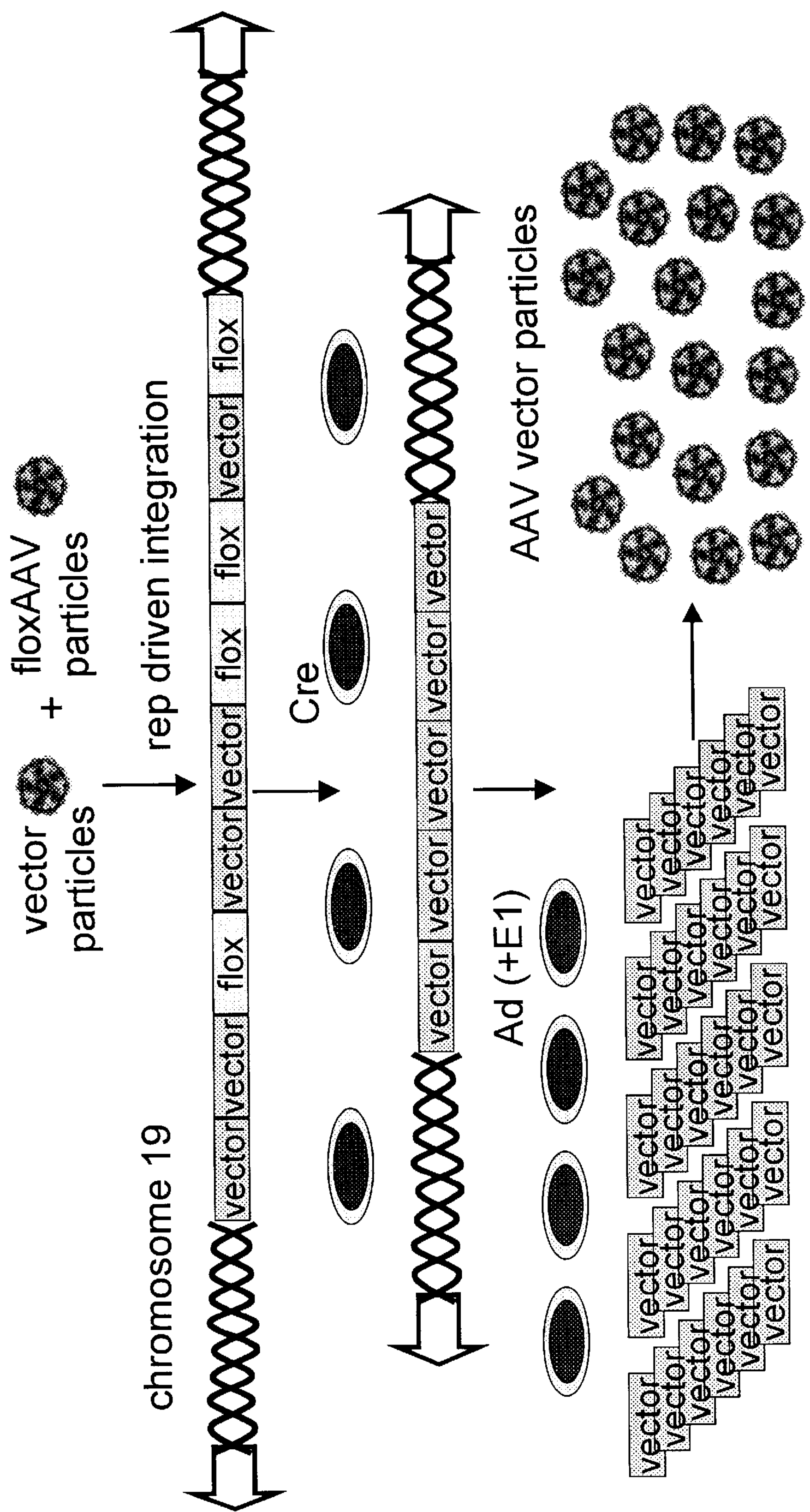
FIG. 2 is a schematic illustration of one representative example of methods for making AAV vector particles utilizing site-specific recombination locus and recombinase such as the Cre—lox system.

The present investors were partially right; no replication competent, infectious wild type AAV, or replication competent rAAV were detected. However, much to the surprise of the present inventor, few AAV capsids were formed. The Cre excised circular rep/cap gene remained inactive, and hence not transcribed. To overcome this inadequacy in the system the present inventor added a second recombinant adenovirus (Ad loxP) to the induction mixture. This second recombinant adenovirus, depicted in FIG. 2, contains an irrelevant gene substitution into the E1 region that is followed by a loxP site. When the new induction mixture depicted in FIG. 2 was introduced into the AAV particle-packaging cell of the present invention, significant production of infectious, replication incompetent rAAV containing the gene of interest was detected. No replication competent rAAV were identified.

Figure 10A:
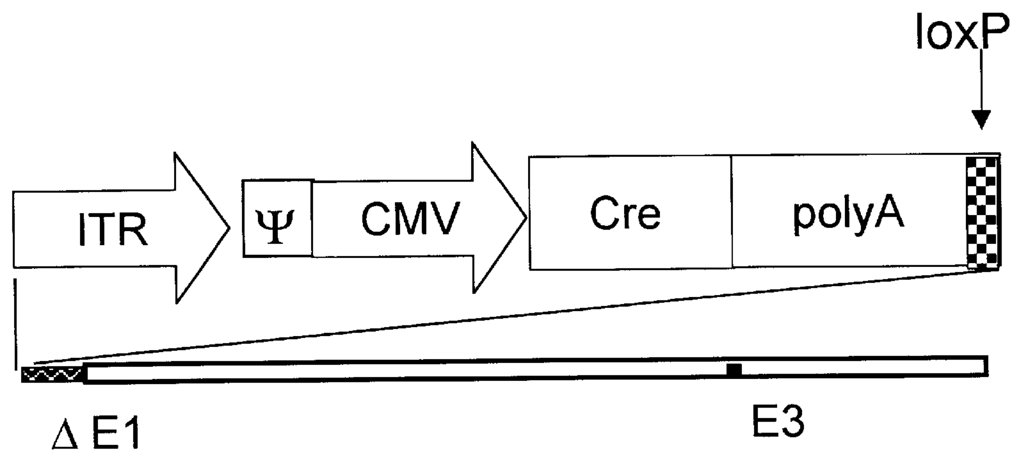
FIG. 10*a* schematically depicts an E1 deleted adenovirus vector expressing Cre recombinase and containing a loxP site.
Figure 10B:
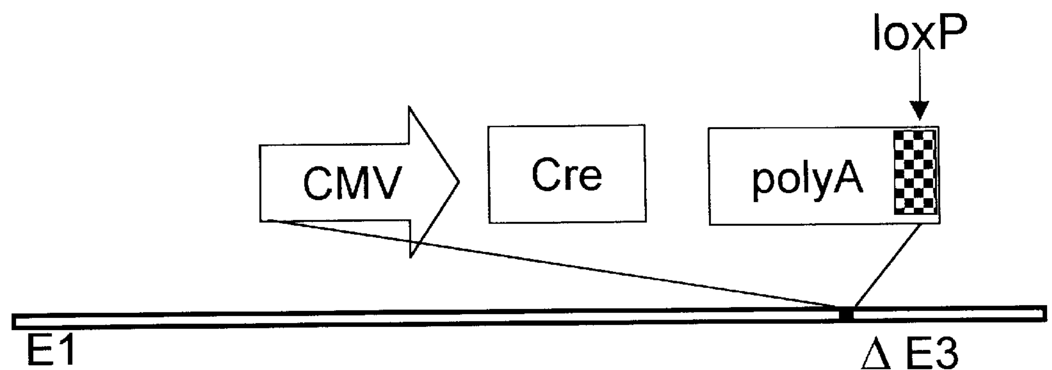
FIG. 10*b* schematically depicts an E3 deleted adenovirus vector expressing Cre recombinase and containing a loxP site.

In another embodiment of the present invention the induction system is composed of a recombinant adenovirus (ΔE1 Cre-loxP Ad) wherein the E1 gene of wild type adenovirus is substituted by plasmid DNA (SEQ. ID. NO 7). The substitution is composed of a CAAV promoter inserted immediately down stream of residue number 550, a Cre sequence down stream of the CAAV promoter at nucleotide residue number 1187–2251 followed immediately by a sequence from SV40 that specifies polyadenylation in mRNA at 2251–2476 and a loxP site at 2476–2520 (See FIG. 10*a*). In another embodiment of the present invention, a similar shuttle plasmid is substituted for the adenovirus E3 gene by standard techniques (see FIG. 10*b*). In this embodiment, full helper function is retained by the recombinant adenovirus (ΔE3 Cre-loxP Ad) in addition to encoding for Cre and having a loxP site capable of activating the excised cap/rep gene from the packaging cell chromosome. The ΔE3 Cre-loxP Ad helper retains E1 gene function making this embodiment a self contained helper/induction system.

The present inventor contend, without being held to nor limited by this theory, that the activation of the inactive Cre excised rep/cap circular DNA requires passage through an adenovirus. The loxP adenovirus of the present invention is provided to the system insufficient number such that the probability of an interaction between Ad loxP and inactive circularized rep/cap is statistically likely. The loxP sites between the Ad loxP and the circularized rep/cap/loxP interact such that the rep/cap genes become active and are expressed forming functional AAV capsids.

The starting point for the above strategy was to create a modified molecular clone of AAV in a plasmid. PCR was used to insert a pair of loxP sites into a rAAV plasmid with 135 base ITR's and a short region of ϕX174 DNA in the left end, and then inserted the rep and cap genes to make pfloxAAV. The 135 base ITR's are missing 10 bases in the D regions. This deletion does not affect the ability of rAAV to be replicated or packaged in transiently transfected 293 cells. Similarly the ϕX 174 DNA should not affect the floxAAV biology, but serves as a marker to differentiate AAV and floxAAV.

Cre Recombinase Reduces flox AAV Titer

Confirmation that the floxAAV strategy was working was obtained by testing the rescue, growth and selection of floxAAV from a plasmid. First 293 cells were transfected with pfloxAAV or a wild type AAV plasmid (pAV2) and then infected with Ad, next low molecular weight DNA was prepared, digested with DpnI and analyzed the DNA by gel electrophoresis. For half the samples Cre8 cells (Cre8 cells are 293 cells that express a high level of Cre recombinase) were used. In 293 cells pfloxAAV produced DpnI resistant DNA that was slightly larger than authentic AAV. In contrast, no detectable floxAAV from Cre8 cells was seen, while AAV was identical to the 293 sample. For a more sensitive view of floxAAV recombination and replication in Cre8 cells, Southern blot analysis of the DNA digested with HindIII or HindIII and DpnI was conducted, and the DNA's were visualized with a rep sequence probe. HindIII cuts AAV once producing 1.8 and 2.8 kb products from linear DNA and longer products from replication intermediates. Replicating floxAAV in Cre containing cells were detected at a very low level. The input plasmid at 8 kb was not detected, but a 4.4 kb species was seen resulting from recombination. Recombination produces a genome length HindIII fragment that migrates slightly faster than genome length wild type AAV since it is missing 350 nucleotides of ITR's and ϕX DNA. Further this 4.4 kb fragment is partially sensitive to DpnI indicating that it is a mixture of recombined plasmid DNA and recombined replicated AAV. These data show that Cre-mediated recombination provides a very efficient selection against floxAAV replication.

Next, the ability of pfloxAAV to make both rAAV and AAV was assessed by comparing pAV2, pfloxAAV and pKS rep/cap as packaging genomes each co-transfected with a rAAV plasmid, pGFP, into 293 or Cre8 cells. The pKS rep/cap plasmid contains the rep and cap genes but no ITR's, while pGFP carries a rAAV with normal 145 base ITR's and CMV immediate early promoter driving expression of enhanced GFP (see FIG. 6). There are two important effects of the modifications in floxAAV relative to AAV. First, comparing the amount of GFP virus packaged by each plasmid in 293 cells, it is of note that pKS rep/cap and pfloxAAV packaged equal amounts of rAAV and that pAV2 packaged less measured either as DNA or GFP transduction activity. This shows that replicating floxAAV supports production of rAAV as well as pKS rep/cap, a plasmid that has no AAV origins. The second affect concerns the amount of AAV in the product. There was a ten times more AAV than floxAAV DNA in the lysates from 293 cells. This difference results from the D10 ITR's on the floxAAV. This conclusion is based partially on the observation similar production of AAV and floxAAV is seen when the floxAAV had 145 base ITR's (data not shown). In Cre8 cells the difference between AAV and floxAAV was increased to 100 fold, showing the combined effects of the Cre selection and D10 deletion. These particle numbers are consistent with the replication data. Interestingly, the same amount of rAAV was packaged by floxAAV in both 293 and Cre8 cells even though the number of AAV genomes available to supply protein dropped substantially.

The present inventor has also determined that the flox AAV genome can be easily carried in a retrovirus vector. Specifically these sequences include the flanking loxP sites and the rep and cap genes, but exclude the AAV ITR's. Thus the fragment inserted into a retrovirus vector is: loxP, rep, cap, loxP. Although either orientation may work, the loxP, rep, cap, loxP fragment should optimally be carried such that the retrovirus promoter and the AAV promoters (p5, p19, p40) face in opposite orientation to avoid interference of the AAV expression signals in making the retrovirus vector. The equivalent vector may also be constructed in a self inactivating vector background by using a suitable deletion in the 3' LTR. Similarly, the same ends maybe achieved through use of a lentivirus vector of fundamentally the same construction (see FIGS. 8*a*–8*d*).

The operational steps to construct and use a floxAAV cell population (line) are similar to the example using AAV ITR's. First, a stock of recombinant retrovirus (rRV) is prepared according to standard techniques. This is infected into suitable cells in the usual manner. These cells are infected with a rAAV genome. Both genomes will integrate into host DNA. The rAAV genome may be added to the cells either before, at the same time or after the rRV infection. Both of these infections may be repeated to increase the frequency of cells carrying the rAAV and rRV genomes. Cells carrying rRV genomes that are largely silent with respect to AAV will grow out. A selectable marker may be included in the rRV to increase the frequency of rRV integrated genomes. After cell expansion, the rAAV is produced by infection with adenovirus and adenovirus vectors carrying Cre and a loxP site. The floxAAV genome will be excised by Cre. It will then be activated by the adenovirus with a loxP site. AAV proteins will then excise, replicate and package the rAAV. Finally the helper viruses will be removed by a combination of heat inactivation and column purification. As noted above, the present invention provides compositions and methods for producing recombinant AAV vector particles.

The infectious, replication incompetent recombinant AAV vector particles (rAAV particles) made according to the teachings of the present invention are ideally suited for expressing polypeptides and/or anti-sense nucleic acids in vivo and in vitro. In one embodiment of the present invention the rAAV particles of the present invention can be used for in vivo or ex vivo gene therapy. For example, and not intended as a limitation, rAAV particles can be used to provide cells with genes encoding for therapeutic polypeptides such as, but not limited to blood coagulation factors such as Factor VII, Factor VIII, Factor IX, and Factor XI. In other embodiments the rAAV particles may provided genes encoding for pathogenic antigens such as, but not limited to hepatitis A virus, hepatitis B virus, hepatitis C virus, human immunodeficiency virus, dengue fever virus, malaria, and numerous other bacterial, viral and/or parasitic antigens. In yet other embodiments the rAAV particles made in accordance with the teachings of the present invention can be provided with genes encoding for cytotoxic protein and anti-sense nucleic acids.

In one embodiment of the present invention the rAAV particles are administered to patients in need of a therapeutic polypeptide. For example, rAVV particles having genes encoding for alpha-1-antitrypsin may be suspended in an physiological solution such as saline that can be administered using an atomizer and directly inhaled into the patient's lungs. In another embodiment a pharmaceutically acceptable carrier containing the therapeutic rAAV particles of the present invention may be administered systemically by intravenous injection. Other means of systemic and/or localized delivery include, but are not limited to transdermally, anal and vaginal suppositories, and orally.

In another embodiment of the present invention the therapeutic rAAV particles of the present invention can be used to introduce genes encoding for polypeptides using ex vivo techniques. For example, and not intended as a limitation, cells such as, but not limited to hematopoietic stem cells can be isolated from a patient's bone marrow using positive or negative selection techniques. The selected cells are then cultured under suitable conditions in vitro and infected with therapeutic rAAV particles. In one embodiment the therapeutic rAAV also contains a selectable marker that permits the detection of cells that have been successfully transformed. These cells are then re-introduced into the patient directly, or expanded in vitro to increase the number of transformed cells prior to re-introduction. Once the transformed cells made in accordance with the teachings of the present invention are returned to the patient, the transformed cells express their gene product in vivo restoring the deficient genes function. Another example of ex vivo gene therapy using the rAAV particles of the present invention involves isolating pancreatic cells from a diabetic patient and transforming them with rAAV particles having genes encoding for insulin. Once the pancreatic cells have been transformed they are re-implanted into the patient such that proper insulin production is restored. Ex vivo techniques using autologous cells reduce the probability of adverse immune responses such as host verses graft disease.

The present invention can also be used to treat or ameliorate cancer in patients by administering rAAV particles that express cytotoxic polypeptides, anti-sense nucleotides or genes that induce apoptosis. In this example, the rAAV particles can be directly injected into the neoplasm or administered systemically if the virus is engineered to specifically target the cancer cell.

Techniques designed to direct rAAV particle target selection in vivo are contemplated as part of the present invention. For example, the AAV cap region can be substituted with a capsid protein from another virus that has an affinity for a particular cell type. For example, the AAV cap region can be substituted with human parvovirus B19 cap genes to increase the vector's affinity for hematopoietic cells. Furthermore, it is also possible to provide the rAAV particle with heterologous viral genes that encode for additional capsid proteins or provide viral envelope genes.

In another embodiment of the present invention the rAAV particles are used to produce recombinant proteins having therapeutic or commercial value in vitro using large scale bioreactors. For example, a bioreactor can be used to grow Hela cells to extremely high numbers, in some cases exceeding $10^8$ cells per mL. Before or after this critical cell mass is obtained, rAAV particles encoding for tissue plasma activator (TPA) are added to the bioreactor and allowed to infect the Hela cells. The Hela cells then express the gene encoding for TPA and produce the protein. Next the recombinant TPA is purified from the bioreactor cellular milieu using techniques known to those of ordinary skill in the art. The purified recombinant TPA is then mixed with a pharmaceutically acceptable carrier and used for therapeutic applications.

It is understood that any number of variations of these examples are possible. For example, various gene expression promoters can be used including inducible promoters. Moreover, temperature sensitive point mutations can be integrated into the rAAV genome that permit thermal gene regulation. In other embodiments of the present invention cell selection markers including but not limited to antibiotic resistance genes may be incorporated in the rAAV particle genome to proved rapid identification and enrichment of transformed cells.

In order to further an understanding of the present invention, a variety of examples are provide below for the purpose of illustrating certain embodiments of the present invention.

EXAMPLES

Example 1

Recombinant AAV Vector Production by Transient Transfection.

In order to demonstrate the effect of Cre recombinase on recombinant AAV (rAAV) vector production and flox AAV growth, mixtures of plasmid DNA's are transfected as calcium phosphate precipitates into either 293 or Cre8 cells (Graham, F. L. and A. J Van Der Eb., A new technique for the assay of infectivity of human adenovirus 5 DNA, *Virology* 52:456–467 (1973)). Both cells are cultured in DMEM with 10% fetal bovine serum (Cre8 cells are 293 cells that produce a high level of Cre recombinase tagged with a nuclear localization sequence (Hardy, S., et al., 1997, J. Virol. 71, 1842–1849).

More specifically, 3 micrograms of an AAV packaging plasmid are combined with 3 micrograms of pCMV GFP, a plasmid with a GFP expressing rAAV genome insertion (SEQ. ID. NO. 1). The plasmids are then mixed with transfection reagents according to Graham and Van der Eb, and applied to $2.5\times10^6$ cells for 6 hours. At this point the media is changed and wild type adenovirus type 5 is added at 10 infectious units per cell. After three days the viral particles are harvested by suspending the cells in their media (5 ml), centrifuging 2 minutes in a clinical centrifuge, resuspending the cells in 0.5 ml of growth media, freezing and thawing the suspension 3 times, and then removing the cell debris by brief centrifugation.

The amount of functional GFP rAAV is determined by infecting $10^6$ 293 cells with 10 $\mu$l of lysate, and then determining the number of GFP expressing cells using fluorescent activated cell scanning at 24 hours after infection. The amount of packaged AAV genomes is determined by a dot blot assay done on 20 $\mu$l of lysate (*Blood,* 1990, 76:1997–2000).

Utilizing the above methods, the following AAV packaging plasmids can be compared: 1. pKSrepcap, a non-replicating control plasmid containing rep and cap genes but no inverted terminal repeats (ITR) (*Human Gene Therapy,* 1998 9:477–485), pAV2 , a plasmid containing a wild type AAV2 genome (SEQ. ID. NO. 2), 3. pfloxAAV, a version of pAV2 with 2 loxP sites inserted such that the loxP sites flank the rep and cap genes and thus separate the ITR's from these genes (SEQ. ID. NO. 3).

The pAV2 plasmid produced mostly AAV and a low yield of GFP vector with no effect of Cre recombinase. In contrast, pfloxAAV packages as much GFP vector as the pKS repcap control plasmid and while the amount of GFP vector is not affected by Cre recombinase, the amount of floxAAV in the product is reduced to 1/10 of the 293 value by the action of Cre recombinase. The changes between pAV2 and pflox-AAV have a further effect. In 293 cells it was evident that the GFP vector did not compete with wild type AAV for replication or packaging, while the GFP vector was able to compete against floxAAV.

Example 2 rAAV Production From Virally Transduced Cells.

A mixed population of floxAAV and GFP vector particles are prepared in 293 cells as described above in Example 1. The adenovirus is inactivated by heat treatment at 56 degrees centigrade for 30 minutes. One thousand HeLa cells are infected with 0.2 ml of the mixed lysate. These cells are expanded for 2 weeks. After 2 weeks, the cells are sorted on a fluorescent activated cell sorter for high GFP expression. The positive population is then expanded. These sorted cells are then used to produce GFP vector particles in the following manner. Briefly, $10^6$ cells are infected with adenovirus plus or minus adenovirus vectors at a multiplicity of 10 infectious units per cell for each type of adenovirus. After 3 days the virus particles are harvested and assayed for functional GFP vector and packaged AAV genomes as described above in Example 1. The adenovirus helpers are the following: (see FIG. 3.) dl 309, a wild type adenovirus (Jones, N. and T. Shenk, 1979, *Cell* 17:683–689), Ad Cre expressing Cre recombinase under control of the CMV immediate early promoter (Anton and F. L. Graham, 1995, J. of Virol. 69:4600–4606), Ad cap2, made by Cre/lox recombination and expressing AAV VP1,2,3 from the CMV immediate early promoter of pAdlox (Hardy, S., et al., 1997, Journal of Virol. 71, 1842–1849). Ad cap contains a loxP site (SEQ. ID. NO. 4).

The Ad Cre and Ad cap viruses had a very dramatic effect on the yield of both GFP vector and floxAAV particles. In particular, infection with 309 produced a high level of both GFP and floxAAV particles as would be expected since 309 induces replication of AAV. Ad Cre should not be able to induce AAV replication since it is missing adenovirus E1 proteins and thus it fails to produce either type of particle. Ad Cre+309 makes a very small amount of GFP vector particles and no detectable floxAAV. Addition of Ad cap to Ad Cre and 309 now produces a high amount of GFP vector particles but no detectable floxAAV.

Example 3 rAAV Production with Split Genome Packaging Vectors.

1. pfloxrep and Modified Ad cap.

The majority of the capsid genes from pfloxAAV are first deleted by deleting sequences between nucleotides 2253 and 4424. The deletion may be made larger by also removing from 4424 to the right hand ITR at 4535. Alternatively, the sequence between nucleotides 2228 and 2253 can be made non-homologous to AAV by altering nucleotides in this region without changing the amino acids of rep 68 protein. Finally, the pfloxrep plasmid can be changed by substituting a foreign 3' splice site between 2186 and 2227 such that the splice site will function with the 5' splice site at 1907 in AAV. The capsid genes will now have to be supplied in trans from Ad cap. As an alternative, Ad cap can be modified by substituting a foreign intron for the AAV intron between 1907 and 2200 in AAV.

2. Stable Transduced Cells.

A mixed population of viral particles is produced as described above in Example 1, except that pfloxrep is substituted for pfloxAAV, and Ad cap in place of 309. The Ad cap virus is then heat inactivated, and this preparation is utilized to infect HeLa cells as described in Example 2. The resultant cells are then expanded in number.

3. rAAV Vector Particle Production.

The expanded cells from above are infected with a mixture of 309, Ad Cre and Ad cap at 10 functional units each per cell. After three days the particles are harvested as described above. These particles will be rAAV vector particles. Assay for wild type AAV is provided below in Example 4.

Example 4

Replication Assay for Wild Type AAV.

One hundred microliters of purified rAAV particles, approximately $10^{13}$ particles/ml, is added to $10^7$ 293 cells with $10^8$ functional units of wild type adenovirus. After 3 days, the viral particles are harvested by suspending the cells in their media, reducing the volume over the cells from 10 ml to 1 ml, and freezing and thawing the preparation 3 times. Adenovirus is then heat inactivated by raising the temperature to 56 degrees centigrade for 30 minutes. The preparation is gently centrifuged in a clinical centrifuge to remove debris. The resultant supernatant is then added to $10^7$ 293 cells, along with $10^8$ units of adenovirus, and incubated for three days. The cells are then suspended in their media and collected by centrifugation. The media is then removed and a Hirt extraction is performed to harvest low molecular weight DNA (Hirt, B., 1967, J. Mol. Biology, 26:365–369). This extract is analyzed for AAV replicative forms by Southern blot analysis after using probes for rep and cap (Samulski, R. J., et al., 1982, PNAS USA. 79:2077–2081). The assay sensitivity is 1 infectious AAV in $10^{12}$.

Example 5

Activation of Stable floxAAV Genomes by the Combined Action of Cre Recombinase and a loxP site.

Cells containing floxAAV and rAAV from Example 2 were infected with a combination of adenovirus helpers as above. Recombinant AAV (GFP) was prepared and assayed as before. This time we used a Cre expressing adenovirus that also contained a loxP site after the expression cassette (Ad Cre loxP). Again infection with 309 induced production of both floxAAV and GFP rAAV. Co-infection with 309 and Ad Cre failed to induce detectable floxAAV and made a trace of GFP. In contrast, co-infection of 309 plus the Ad Cre bearing a loxP site induced 44% of the GFP that 309 alone did without inducing floxAAV production. The present inventor also obtained the same result using a combination of 309, Ad Cre and a third adenovirus expressing an irrelevant gene followed by a loxP site (see FIG. 5).

Example 6

Excised AAV Genome Recombines into Ad loxP.

Figure 7:
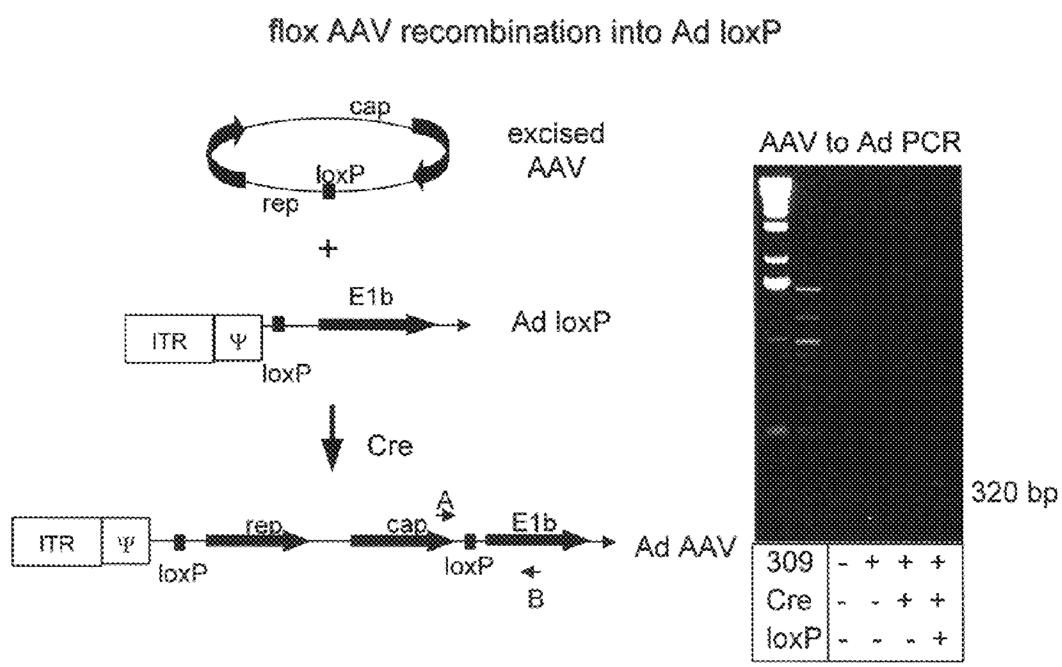
FIG. 7 schematically depicts flox AAV recombination into Adenovirus.
Figure 8A:
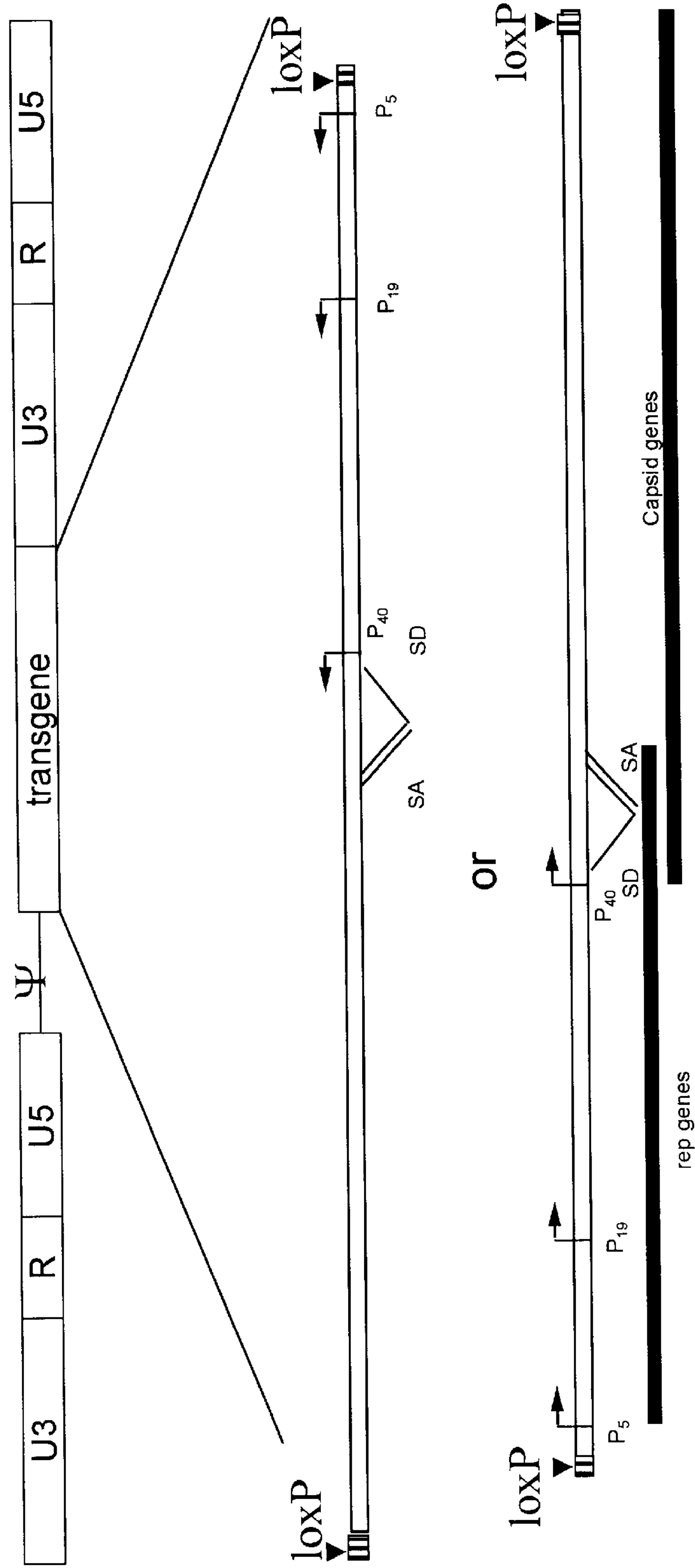
FIGS. 8*a–d* schematically depict representative recombinant retrovirus genomes for use in accordance with the teachings of the present invention.
Figure 8B:
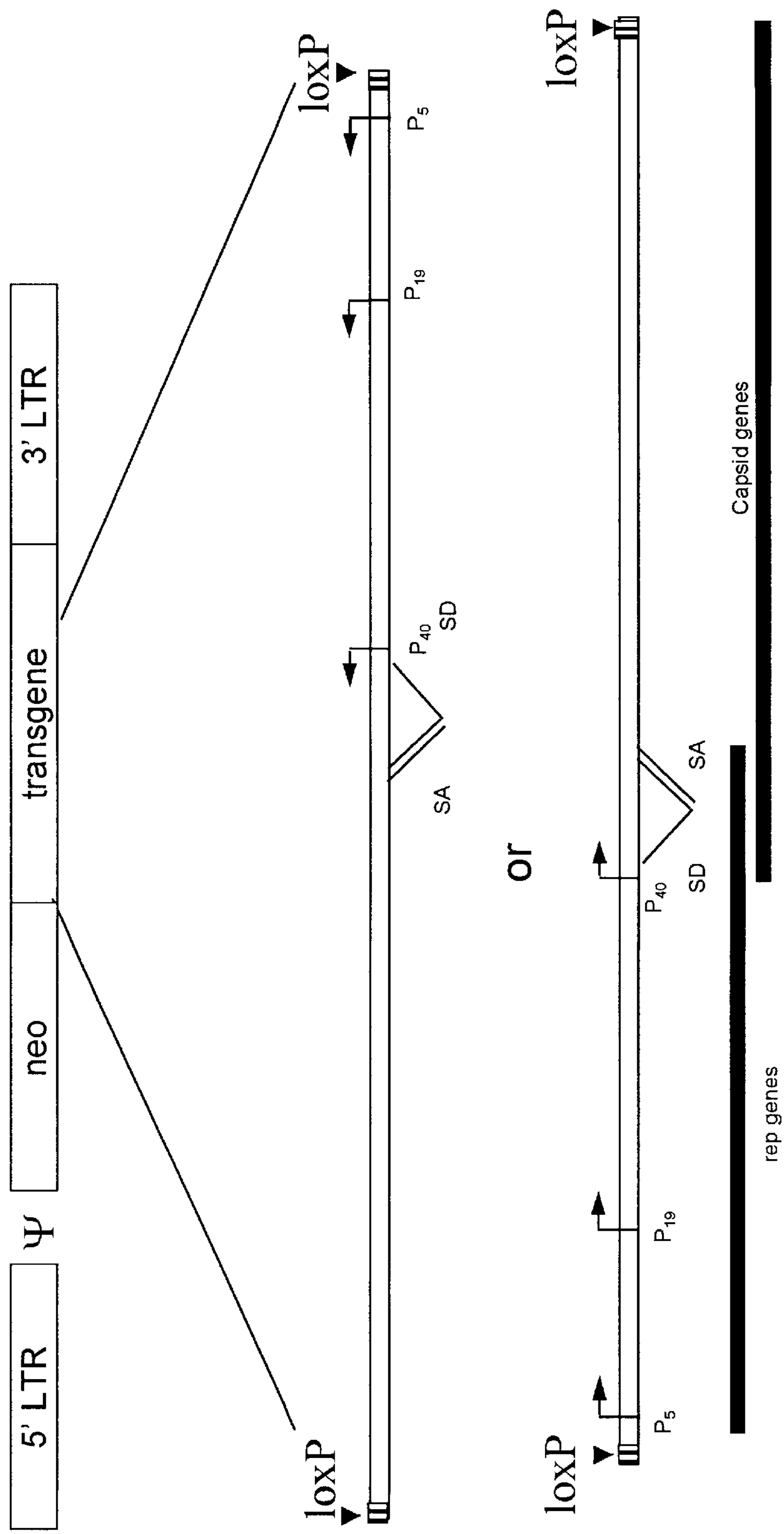
Figure 8C:
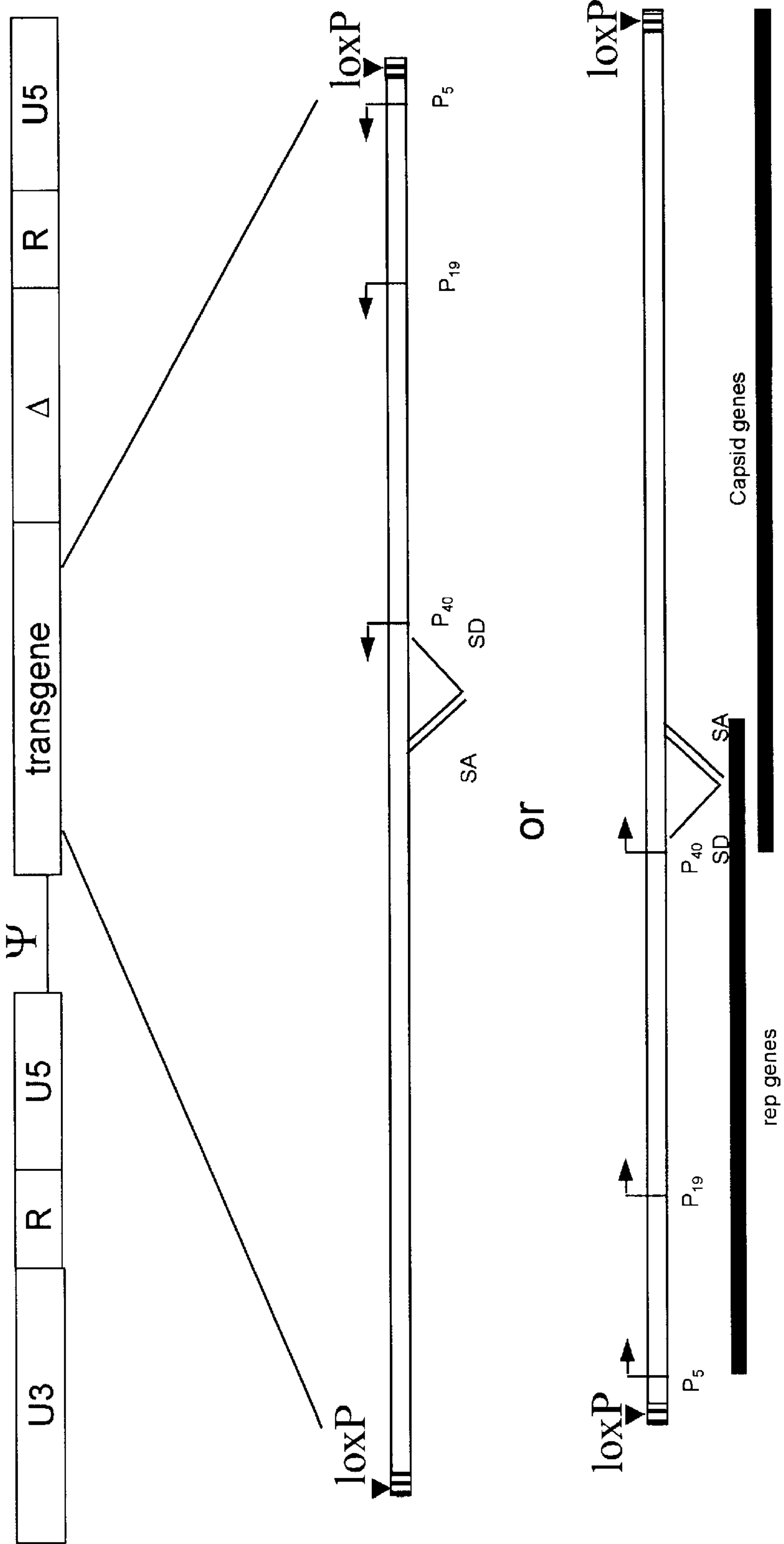
Figure 8D:
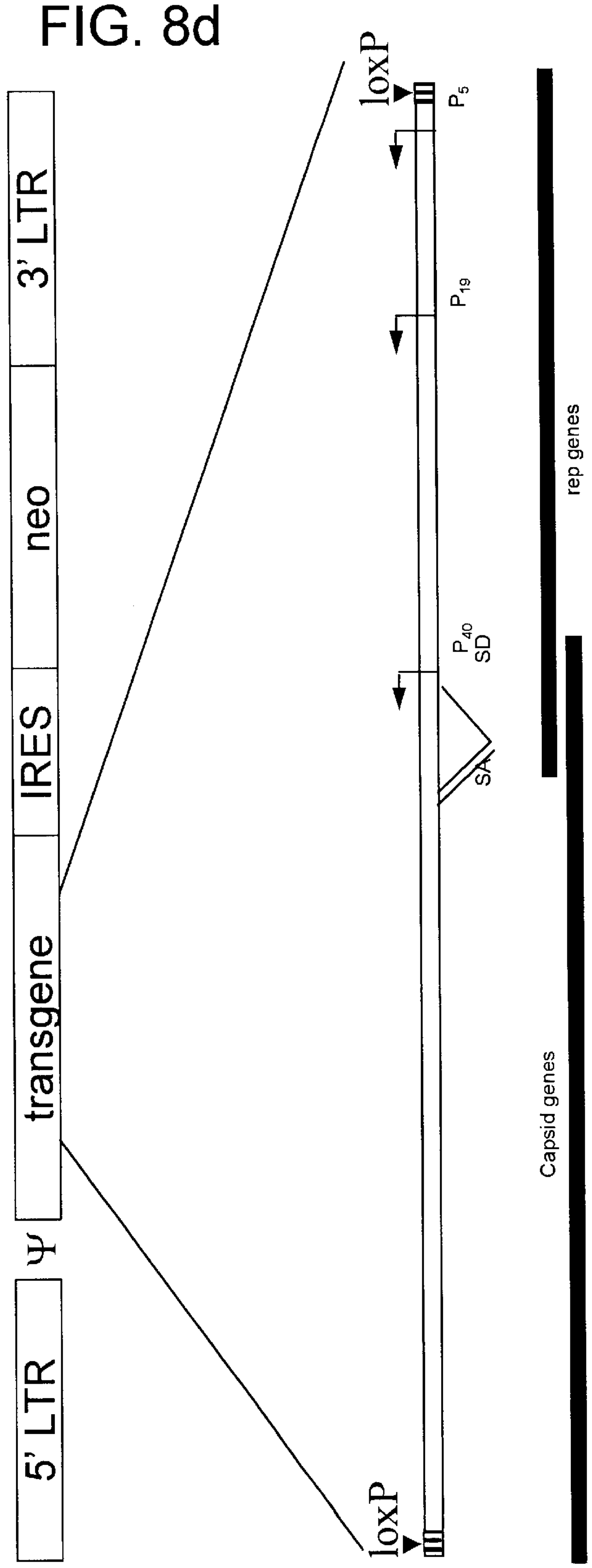

$10^6$ Cells from example 2 were infected with either 309; 309+Ad Cre; or 309+Ad Cre loxP. At 24 hours after infection low molecular weight DNA was extracted according to Hirt (Hirt, B. 1967, J. Mol. Biology. 26:365–369). One percent of each DNA sample was analyzed for specific integration of AAV sequences into adenovirus at the loxP site by PCR according to standard techniques. The first primer located in the cap gene matches the transcribed strand of AAV and is situated just upstream of the loxP site in floxAAV (AAV4449: CCCGGATccgtttaattcgtttcagtt (SEQ. ID. NO. 5)), and the second primer matches the bottom strand of adenovirus in the E1B region and is directed toward the loxP site placed at 3328 in adenovirus (Ad −3511: CCTCAATCTGTATCTTCATC (SEQ. ID. NO. 6)). PCR conditions were: 28 cycles at 94° for 30s, 60° for 45s, and 72° for 30s. Only the reaction with 309+Ad Cre loxP produced the diagnostic 320 nucleotide fragment (See FIG. 7).

Example 7

Packaging of rAAV Using Retrovirus Based floxAAV Cells.

The generation of recombinant retrovirus (rRV) particles have been described (Pear, W S et al., Proc. Natl. Acad. Sci. USA, 90:8392–8396). A retrovirus equivalent of floxAAV (RVfloxAAV) will maintain the same essential features except that the AAV ITR's will be replaced with retrovirus long terminal repeats (LTR's) or their functional equivalent in both plasmids and their integrated proviral forms (for functional equivalents, see: Julius, M A et al., Biotechniques 28: 703). This is done by inserting an AAV fragment: loxP, a rep expressing sequence, a cap expressing sequence, and a second loxP site, into the suitable position in a rRV plasmid. Optimally the AAV promoters are inserted such that they face the opposite direction relative to the LTR's. rRV particles are prepared by standard techniques. Actively growing HeLa cells are infected with the RVfloxAAV at high moi to ensure multiple infection. These cells are then expanded. The expanded cells are infected with rAAV, 309 and Ad Cre loxP. rAAV production is measured as above. Alternatively, the cells containing RVfloxAAV provirus are infected with rAAV particles corresponding to a vector selected for production. These resulting cells carrying both rAAV and RVfloxAAV are then expanded to a suitable number and infected with adenovirus carrying the helper functions plus Cre and a loxP site. At any point the cells infected with RVfloxAAV or combined RVfloxAAV and rAAV may be subcloned to improve titer. The floxAAV genome will be activated by the loxP adenovirus and there by rescue, replicate and package the rAAV genome. Since the floxAAV genome lacks AAV ITR's, there is no possibility of wild type like floxAAV (see FIGS. 8 *a–d*)

Example 8

Analysis of Cre Mediated Excision.

Figure 9:
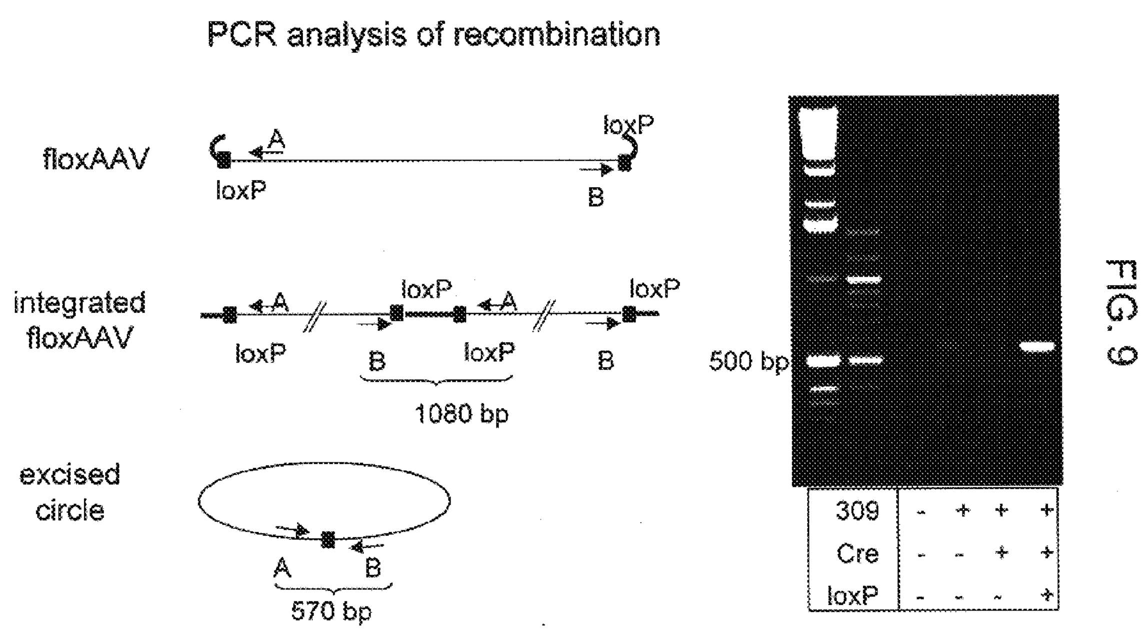
FIG. 9 schematically depicts floxAAV genome and Cre mediated excision and supporting PCR analysis confirming the formation of circular extra chromosomal DNA.

$10^6$ Cells from example 2 were infected with either 309; 309+Ad Cre; or 309+Ad Cre loxP. At 24 hours after infection low molecular weight DNA was extracted according to Hirt (Hirt, B. 1967, J. Mol. Biology. 26:365–369). One percent of each DNA sample was analyzed for excised circular AAV DNA by PCR according to standard techniques as known to those of ordinary skill in the art. The present inventor used a primer in rep on the untranscribed strand (AAV −556: CCCGGAtcccttctcaaattgcacaa (SEQ. ID. NO. 8)) and a second primer in cap on the transcribed strand (AAV 4449: CCCGGATccgtttaattcgtttcagtt (SEQ. ID. NO. 5)). This pair of primers faces away from each other and consequently does not amplify linear AAV. They do amplify circular floxAAV and tandem copies of AAV resulting from replication. 309 infection induced fragments from replication and recombination between the loxP sites that can occur in the absence of Cre. 309 plus Ad Cre produced only the fragment from circular floxAAV. Similarly, 309 plus Ad Cre loxP makes slightly more of the excised circular fragment. Conditions: 25 cycles of 94° C. for 30s, 55° C. for 45s and 72° C. for 60s (see FIG. 9).

The present invention provides compositions and methods for producing rAAV packaging cell lines and high-titer, replication incompetent rAAV preparations. From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A recombinant virus comprising: a 5' adeno-associated virus (AAV) ITR sequence, a first site specific recombination locus, an AAV rep gene sequence, an AAV cap gene sequence, a second site specific recombination locus which combines with said first site specific recombination locus, and a 3' AAV ITR sequence.

2. A recombinant virus comprising: a 5' retrovirus long terminal repeat (LTR) sequence, a retrovirus packaging signal, a site specific recombination locus, an AAV rep gene sequence, an AAV cap gene sequence, a second site specific recombination locus which combines with said first site specific recombination locus, and a 3' retrovirus LTR sequence.

3. The recombinant virus of claim 1 or 2 wherein said first site-specific recombination locus is loxP.

4. The recombinant virus of claim 1 or 2 wherein said second site-specific recombination locus is loxP.

5. A plasmid, comprising a DNA sequence of the recombinant virus according to claim 1 or 2.

6. The recombinant virus of claim 2 wherein retrovirus promoters and AAV promoters face in opposite direction.

7. An adeno-associated virus (AAV) packaging cell comprising: a cell stably carrying an AAV genome, said AAV genome having, a first site-specific recombination locus, an AAV gene rep sequence, an AAV cap gene sequence, and a second site-specific recombination locus.

8. The AAV packaging cell of claim 7 further comprising a first origin of replication flanking said first site-specific recombination locus and a second origin of replication flanking said second site-specific recombination locus wherein said first origin of replication and said second origin of replication replicates nucleic acid sequences there between.

9. The AAV packaging cell of claim 7 or 8 wherein said first origin of replication and said second origin of replication are selected from the group consisting of AAV ITR sequences, retrovirus LTR sequences and combinations thereof.

10. An adeno-associated virus (AAV) packaging cell comprising: an eukaryotic cell stably carrying an AAV genome having a 5' AAV inverted terminal repeat (ITR) sequence, a rep gene sequence, a cap gene sequence and a 3' AAV ITR sequence wherein a first site specific recombination locus is inserted between said 5' AAV ITR sequence and said rep gene sequence and a second site specific recombination locus is inserted between said cap gene sequence and said 3' AAV ITR sequence.

11. An adeno-associated virus (AAV) packaging cell comprising: an eukaryotic cell stably carrying a viral genome having, in order, a 5' retrovirus long terminal repeat (LTR), sequence, a retrovirus packaging signal, a first site specific recombination locus, an AAV rep gene sequence, an AAV cap gene sequence, a second site specific recombination locus and a 3' retrovirus LTR sequence.

12. The AAV packaging cell of claim 11 wherein said order of said AAV rep gene sequence and said AAV cap gene sequence is inverted relative to the LTR.

13. The AAV packaging cell according to claims 10 or 11 wherein said eukaryotic cell is mammalian cell.

14. The AAV packaging cell according to any of claim 7, 10 or 11 wherein said first site-specific recombination locus and said second site-specific recombination locus are loxP sites.

15. The AAV packaging cells according to claims 7 or 10 further comprising a second stably carried AAV genome wherein said second stably carried AAV genome is a recombinant AAV genome having a gene of interest substituted for said recombinant AAV genome's rep and cap gene sequences.

16. The AAV packaging cells according to claims 11 further comprising a second stably carried viral genome wherein said second stably carried viral genome is a recombinant AAV genome having a gene of interest substituted for said recombinant AAV genome's rep and cap gene sequences.

17. A method for producing a recombinant AAV packaging cell comprising:

providing a eukaryotic host cell; and stably infecting said eukaryotic host cell with a recombinant AAV vector, said recombinant AAV vector having an AAV genome comprising a 5' AAV ITR sequence, a first site specific recombination locus, a rep gene sequence, a cap gene sequence, a second site specific recombination locus and a 3' AAV ITR sequence.

18. A method for producing a recombinant AAV packaging cell comprising:

providing a eukaryotic host cell; and stably infecting said eukaryotic host cell with a recombinant retrovirus vector, said recombinant retrovirus vector having a viral genome comprising a 5' retrovirus long terminal repeat (LTR) sequence, a retrovirus packaging signal, a first site specific recombination locus, a rep gene sequence, a cap gene sequence, a second site specific recombination locus and a 3' retrovirus LTR sequence.

19. The method according to claim 17 or 18 wherein said first site specific recombination locus and said second site-specific locus are loxP sites.

20. The method according to claim 17 or 18 wherein said eukaryotic host cell is a mammalian cell.

21. The method according to claim 18 wherein said AAV rep gene sequence and said AAV cap gene sequence are inverted relative to each other.

22. The AAV packaging cells according to claims 17 further comprising a second stably carried AAV genome wherein said second stably carried AAV genome is a recombinant AAV genome having a gene of interest substituted for said recombinant AAV genome's rep and cap gene sequences.

23. The AAV packaging cells according to claims 18 further comprising a second stably carried viral genome wherein said second stably carried viral genome is a recombinant AAV genome having a gene of interest substituted for said recombinant AAV genome's rep and cap gene sequences.

24. A method for producing recombinant AAV vector particles comprising:

providing an eukaryotic host cell;

stably infecting said eukaryotic host cell with a first recombinant AAV vector, said first recombinant AAV vector having an AAV genome comprising a 5' AAV ITR sequence, a first site specific recombination locus, an AAV rep gene sequence, an AAV cap gene sequence, a second site specific recombination locus and a 3' AAV ITR sequence;

stably infecting said eukaryotic host cell with a second recombinant AAV vector, said second recombinant AAV vector having an AAV genome comprising a 5' AAV ITR sequence, a heterologous gene of interest, and a 3' ITR sequence;

infecting said eukaryotic host cell with a helper virus selected from the group consisting of adenovirus and herpes virus;

infecting said eukaryotic host sell with a recombinant vector selected from the group consisting of an adenovirus expressing Cre, an adenovirus with an integrated loxP site, an adenovirus expressing Cre and having an integrated loxP site, a herpes virus expressing Cre, a herpes virus having an integrated loxP site, and a herpes virus expressing Cre and having an integrated loxP site; and recovering said recombinant AAV vector particles from said eukaryotic host cell.

25. A method for producing recombinant AAV vector particles comprising:

providing an eukaryotic host cell;

stably infecting said eukaryotic host cell with a recombinant retrovirus vector, said retrovirus vector having a genome comprising a 5' retrovirus LTR sequence, a non-coding nucleic acid sequence, a first site specific recombination locus, an AAV rep gene sequence, an AAV cap gene sequence, a second site specific recombination locus and a 3' retrovirus LTR sequence;

stably infecting said eukaryotic host cell with a second recombinant AAV vector, said second recombinant AAV vector having an AAV genome comprising a 5' AAV ITR sequence, a heterologous gene of interest, and a 3' ITR sequence;

infecting said eukaryotic host cell with a helper virus selected from the group consisting of adenovirus and herpes virus;

infecting said eukaryotic host sell with a recombinant vector selected from the group consisting of an adenovirus expressing Cre, an adenovirus with an integrated loxP site, an adenovirus expressing Cre and having an integrated loxP site, a herpes virus expressing Cre, a herpes virus having an integrated loxP site, and a herpes virus expressing Cre and having an integrated loxP site; and recovering said recombinant AAV vector particles from said eukaryotic host cell.

26. A method for producing recombinant AAV vector particles comprising:

providing an eukaryotic host cell;

stably infecting said eukaryotic host cell with a first recombinant AAV vector, said first recombinant AAV vector having an AAV genome comprising a 5' AAV ITR sequence, a first site specific recombination locus, a AAV rep gene sequence, an AAV cap gene sequence, a second site specific recombination locus and a 3' AAV ITR sequence;

stably infecting said eukaryotic host cell with a second recombinant AAV vector, said second recombinant AAV vector having an AAV genome comprising a 5' AAV ITR sequence, a heterologous gene of interest, and a 3' ITR sequence;

infecting said eukaryotic host cell with a recombinant adenovirus AdCre such that said AdCre produces recombinant Cre is sufficient quantities to excise said AAV rep gene sequence and said AAV cap gene sequence together in an inactive circular form from said first recombinant AAV genome;

infecting said eukaryotic host cell with a recombinant adenovirus AdloxP wherein said AdloxP activates said excised inactive circular form of said AAV rep gene sequence and said AAV cap gene sequence;

infecting said eukaryotic host cell with a helper virus selected from the group consisting of adenovirus and herpes virus; and recovering said recombinant AAV vector particles from said eukaryotic host cell.

27. A method for producing recombinant AAV vector particles comprising:

providing an eukaryotic host cell;

stably infecting said eukaryotic host cell with a recombinant retrovirus vector, said retrovirus vector having a genome comprising a 5' retrovirus LTR sequence, a non-coding nucleic acid sequence, a first site specific recombination locus, an AAV rep gene sequence, an AAV cap gene sequence, a second site specific recombination locus and a 3' retrovirus LTR sequence;

stably infecting said eukaryotic host cell with a second recombinant AAV vector, said second recombinant AAV vector having an AAV genome comprising a 5' AAV ITR sequence, a heterologous gene of interest, and a 3' ITR sequence;

infecting said eukaryotic host cell with a recombinant adenovirus AdCre such that said AdCre produces recombinant Cre is sufficient quantities to excise said AAV rep gene sequence and said AAV cap gene sequence together in an inactive circular form from said first recombinant AAV genome;

infecting said eukaryotic host cell with a recombinant adenovirus AdloxP wherein said AdloxP activates said excised inactive circular form of said AAV rep gene sequence and said AAV cap gene sequence;

infecting said eukaryotic host cell with a helper virus selected from the group consisting of adenovirus and herpes virus; and recovering said recombinant AAV vector particles from said eukaryotic host cell.

28. A method for producing recombinant AAV vector particles; comprising:

(a) introducing into a host cell (i) pfloxAAV, (ii) a recombinant AAV vector encoding plasmid, and (iii) a plasmid encoding herpesvirus, cytomegalovirus, or adenoviral functions, or a herpesvirus, cytomegalovirus, or, adenovirus itself, in order to produce flox AAV particles and recombinant AAV particles;

(b) introducing into a second host cell (i) the recombinant AAV particles and flox AAV particles of (a), (ii) a vector which directs the expression of Cre, and (iii) a vector which directs the expression of herpesvirus, CMV, or adenovirus helper functions, such that said recombinant AAV vector particles are produced.

29. A host cell, comprising an integrated DNA sequence of the recombinant adeno-associated virus according to claim 1.

30. The host cell according to claim 6, further comprising a recombinant AAV vector.

31. Circular DNA, comprising rep and cap genes, wherein said circular DNA does not have a bacterial or eukaryotic origin of replication.

32. A method for the intracellular activation of an inactive extra-chromosomal AAV rep/cap circular DNA fragment having a loxP site comprising:

providing a recombinant AdloxP vector to a cell having said inactive extra-chromosomal AAV rep/cap circular DNA fragment having said loxP site; and infecting said cell with a helper virus.

33. A recombinant adeno-associated cap (−) virus, comprising, 5' AAV ITR sequence, a first site specific recombination locus, the rep genes, a second site specific recombination locus which recombines with said first site specific recombination locus, and a 3' AAV ITR sequence, with the proviso that said recombinant adeno-associated cap (−) virus does not contain any functional cap genes.

34. The recombinant adeno-associated cap(−) virus according to claim 33, further comprising a poly(A) sequence.

35. A plasmid, comprising the DNA sequence of the recombinant adeno-associated virus according to claim 33.

36. An AAV helper virus comprising;

an E1 deleted adenovirus having a Cre gene and a loxP site inserted into said E1 deleted adenovirus genome.

37. The AAV helper virus of claim 36 wherein said Cre gene in under the control of a CMV promoter.

38. The AAV helper virus according to claim 36 wherein said loxP site is inserted downstream of a polyA sequence.

39. An AAV helper virus comprising;

an E3 deleted adenovirus having a Cre gene and a loxP site inserted into said E3 deleted adenovirus genome.

40. The AAV helper virus of claim 39 wherein said Cre gene in under the control of a CAAV promoter.

41. The AAV helper virus according to claim 39 wherein said loxP site is inserted downstream of a polyA sequence.

42. An adeno-associated virus (AAV) packaging cell comprising:

a cell stably carrying a first AAV genome, said first AAV genome having, a first site-specific recombination locus, an AAV gene rep sequence and a second site-specific recombination locus; and a second AAV genome, said second AAV genome having, a first site-specific recombination locus, an AAV gene cap sequence and a second site-specific recombination locus.

43. An adeno-associated virus (AAV) packaging cell comprising:

an eukaryotic cell stably carrying a first AAV genome having a 5' AAV inverted terminal repeat (ITR) sequence, a rep gene sequence and a 3' AAV ITR sequence wherein a first site specific recombination locus is inserted between said 5' AAV ITR sequence and said rep gene sequence and a second site specific recombination locus is inserted between said rep gene sequence and said 3' AAV ITR sequence; and second AAV genome having a 5' AAV inverted terminal repeat (ITR) sequence, a cap gene sequence and a 3' AAV ITR sequence wherein a first site specific recombination locus is inserted between said 5' AAV ITR sequence and said cap gene sequence and a second site specific recombination locus is inserted between said cap gene sequence and said 3' AAV ITR sequence.

44. An adeno-associated virus (AAV) packaging cell comprising:

an eukaryotic cell stably carrying a first viral genome having, in order, a 5' retrovirus long terminal repeat (LTR), sequence, a retrovirus packaging signal, a first site specific recombination locus, an AAV rep gene sequence, a second site specific recombination locus and a 3' retrovirus LTR sequence; and a second viral genome having, in order, a 5' retrovirus long terminal repeat (LTR), sequence, a retrovirus packaging signal, a first site specific recombination locus, an AAV cap gene sequence, a second site specific recombination locus and a 3' retrovirus LTR sequence.

45. The AAV packaging cell of claim 44 wherein said order of said AAV rep gene sequence and said AAV cap gene sequence is inverted relative to the LTR.

46. The AAV packaging cell according to claims 43 or 44 wherein said eukaryotic cell is mammalian cell.

47. The AAV packaging cell according to any of claim 42, 43 or 44 wherein said first site-specific recombination locus and said second site-specific recombination locus are loxP sites.

48. The AAV packaging cells according to claims 42 or 43 further comprising a second stably carried AAV genome wherein said second stably carried AAV genome is a recombinant AAV genome having a gene of interest substituted for said recombinant AAV genome's rep and cap gene sequence.

49. The AAV packaging cells according to 44 further comprising a second stably carried viral genome, wherein said second stably carried viral genome is a recombinant AAV genome having a gene of interest substituted for said recombinant AAV genome's rep and cap gene sequences.

* * * * *